US006458146B1

(12) United States Patent
Kramer

(10) Patent No.: US 6,458,146 B1
**(45) Date of Patent: *Oct. 1, 2002**

(54) ACUPUNCTURE TREATMENT DEVICE AND METHODS OF USE

(75) Inventor: George H. Kramer, Minnetonka, MN (US)

(73) Assignee: East West Medical, LLP, Wayzata, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/514,718

(22) Filed: Feb. 28, 2000

Related U.S. Application Data

(63) Continuation-in-part of application No. 09/177,215, filed on Oct. 22, 1998, now Pat. No. 6,030,408.

(51) Int. Cl.[7] .......... A61B 17/04

(52) U.S. Cl. .......... 606/204; 606/189

(58) Field of Search .......... 606/204, 201, 606/189; 63/14.3; 604/290

(56) References Cited

U.S. PATENT DOCUMENTS

| | | | | | |
|---|---|---|---|---|---|
| 3,866,597 | A | | 2/1975 | Boxer | 128/1 R |
| 3,886,939 | A | | 6/1975 | Boxer | 128/268 |
| 3,901,234 | A | | 8/1975 | Yazawa | 128/268 |
| 3,987,787 | A | | 10/1976 | Boxer | 128/1 R |
| 4,022,189 | A | | 5/1977 | Boxer | 128/1 R |
| 4,073,296 | A | | 2/1978 | McCall | 128/303 R |
| 4,098,277 | A | | 7/1978 | Mendell | 128/303 R |
| 4,391,270 | A | | 7/1983 | Uragami | 128/1.3 |
| 5,247,946 | A | | 9/1993 | Holder | 128/864 |
| 5,250,067 | A | | 10/1993 | Gelfer et al. | 606/189 |
| 5,366,475 | A | * | 11/1994 | Voss et al. | 606/204 |
| 5,405,357 | A | | 4/1995 | Rowe-Lanzisera et al. | 606/204 |
| 5,735,143 | A | * | 4/1998 | Tanaka | 63/14.3 |
| 5,792,176 | A | | 8/1998 | Chang | 606/204 |
| 6,030,408 | A | | 2/2000 | Kramer | 606/204 |

FOREIGN PATENT DOCUMENTS

| | | | |
|---|---|---|---|
| DE | 19816282 | 11/1998 | A43B/17/00 |
| EP | 0100050 | 2/1984 | A61H/39/00 |
| FR | 2571613 | 4/1986 | A61H/39/04 |
| JP | 11042268 | 2/1999 | A61H/39/04 |
| WO | 00/23035 | 4/2000 | A61H/39/04 |

OTHER PUBLICATIONS

National Institutes of Health Consensus Development Conference Statement, 107. *Acupuncture*, http://odp.od.nih.gov/consensus, pp. 1–30, (Nov. 3–5, 1997).

* cited by examiner

*Primary Examiner*—Gary Jackson
(74) *Attorney, Agent, or Firm*—Schwegman, Lundberg, Woessner & Kluth, P.A.

(57) ABSTRACT

The present invention provides an acupressure device for use on a selected skin surface portion of a human body. The device comprises a base sheet; one or more protrusions; a fastener; and an orienting margin, orienting constellation, orienting template or orienting protrusion, suitable to position the device on the selected skin surface. The invention also provides therapeutic methods comprising applying a devise of the invention to a human in need of therapy.

44 Claims, 23 Drawing Sheets

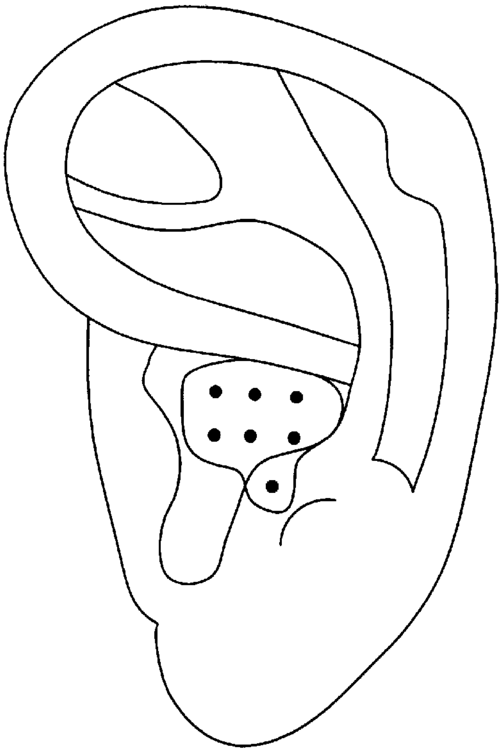
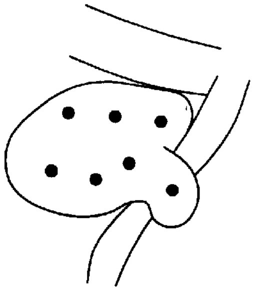
FIG. 38A
FIG. 38B
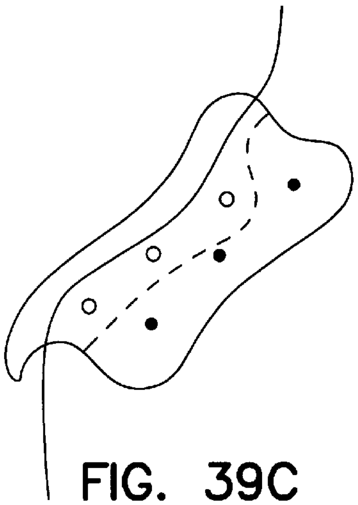
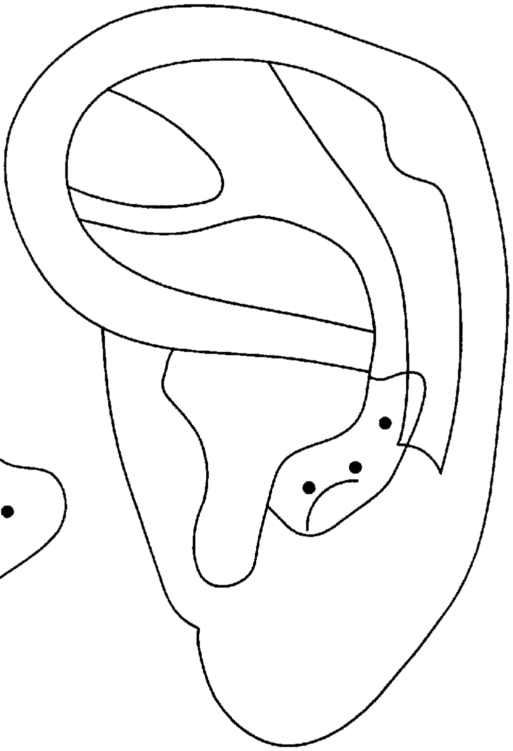
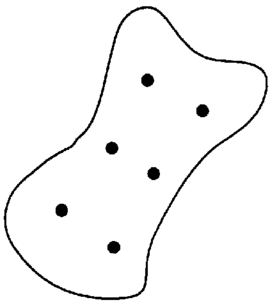
FIG. 39A
FIG. 39C
FIG. 39B

ACUPUNCTURE TREATMENT DEVICE AND METHODS OF USE

CROSS REFERENCE TO RELATED APPLICATIONS

This application is a continuation-in-part of U.S. application Ser. No. 09/177,215 filed Oct. 22, 1998 now U.S. Pat. No. 6,030,408, which is herein incorporated by reference.

FIELD OF THE INVENTION

The present invention relates to an acupressure device, and, in particular, to an acupressure device having an orienting peripheral margin, an orienting template, or an orienting constellation to allign or key the device to specific landmarks of the human body.

BACKGROUND OF THE INVENTION

Acupressure, as with acupuncture, is a form of treatment for various conditions and maladies. Acupuncture is well known to eastern medical thought and practice, but only recently is introduced into western medicine. Acupuncture can be traced back at least 2,500 years as a form of medical treatment in China. The concept behind acupuncture is based on the premise there are patterns of energy flow through the body that are essential for proper health. Imbalance or disruption of energy flow through any of these patterns is believed to be responsible for disease. Which pattern is disrupted, and where, influences which disease state is experienced by the afflicted person.

The energy flow patterns through the body have been mapped extensively and there are substantial numbers of points along the flow patterns where the energy flow is close to the skin surface. Using needles of various types, the acupuncturist is able to reach these points by placing the needles into the skin at these known points. The presence of the needle at that point alters the flow of energy, changing the dynamics in the energy flow. When done properly, using the proper number and position of needles, acupuncture re-aligns the energy flow to one of balance and restoration of health.

The pattern of energy flow disruption is identifiable to the type of disease that the patient presents with. The acupuncturist determines the ailment complained of which then identifies the energy flow imbalance. The energy flow imbalance is then corrected by placing one or more needles into the appropriate points that are associated with the type of energy flow imbalance corresponding to the disease.

The National Institutes of Health Consensus Development Statement on Acupuncture, No. 107, Nov. 3–5, 1997, concluded that acupuncture was an effective therapy for certain medical conditions, especially those involving nausea and pain and should be integrated into standard medical practice. In particular, headaches, nausea, menstrual cramps, low back pain and dental analgesia were some of the medical conditions acupuncture was considered useful for.

The most common use for acupuncture in the U.S. is pain, with headache as the most frequent complaint in doctors' offices review of symptoms, and the most frequent reason for use of over-the-counter medications. U.S. and Chinese studies have shown acupuncture and acupressure therapy are useful for treating pain.

Acupuncture and acupressure have also been used successfully in the treatment of a wide variety of other medical and health related conditions. For example, these techniques have been shown to be useful for relieving post-opperative nausea and for alleviating the symptoms associated with drug withdrawal.

Thus, acupressure therapy is a simple inexpensive technique, with virtually no negative side effects, that could greatly enhance the treatment of many health conditions if it were readily available to the lay public.

Acupressure is a direct offshoot of acupuncture wherein one or more known points on the surface of the skin receive pressure instead of having a needle inserted. The concept remains the same, re-institute balanced energy flow as treatment of a malady caused by an imbalance in the energy flow through the body. Western medical research has also shown physiological effects, including reflexes and neurohumoral effects of acupuncture and acupressure in human subjects.

Acupuncture and acupressure points are at anatomically defined areas of the skin along 12 meridians, or lines of energy flow. In addition, further research has determined that there are several areas on the surface of the skin where the entire body is represented as a homunculus. Several areas incorporating a homunculus representation are the ears, hands, and soles of the feet. Acupuncture and acupressure to portions of the ear, hand, or sole of the foot effects a corrective energy or reflex change in the part of the body represented by that part of the homunculus.

Several acupressure devices are known in the art, for example, see U.S. Pat. Nos. 3,866,597; 3,886,939; 3,987,787; and 4,022,189, and all issued to Boxer. The devices disclosed make use of one or more small rigid objects that are applied by the user to one or more particular points of the user's body. The devices disclosed are either square or rectangular in shape and they either have a single small object in the center or several spread randomly across the surface of the device. Each of these devices requires that either the user or a helper have considerable knowledge and experience in determining where and how to place the objects on the user's skin. U.S. Pat. No. 3,901,234 issued to Yazawa discloses a similar device to that of Boxer, but adds a medicated adhesive layer.

U.S. Pat. No. 4,098,277 issued to Mendell discloses a custom molded, and expensive, device for use in a person's ear that bears one or more blunt protrusions of the mold surface as acupressure points. Such a device is limited to use by only the person for which the device is molded and requires skilled help in fabricating the device. Placement of the acupressure points on the device is permanent. A single patient would require any number of individual custom molded devices, each device having a different pattern of acupressure points corresponding to treatment of differing maladies, in order to treat the different maladies that one person may encounter over time.

Another device is disclosed in U.S. Pat. No. 4,073,296 issued to McCall wherein the device is a custom molded piece, again for a single individual's ear. This device incorporates nodules inserted into the surface of the molded device to achieve the acupressure effect. Like the Mendell device, this device requires one of high skill to construct the device for proper fit and each mold can only treat the one specific malady intended.

What is needed is a device that is relatively inexpensive, which can be applied by the user without need to involve an expert in acupressure in the process. Each devise should be keyed to a particular anatomical surface shape that is readily identifiable to the user, thus providing easy accurate placement of the acupressure device.

SUMMARY OF THE INVENTION

The present invention includes an acupressure device for use on a selected skin surface portion of a human body. The device is keyed (e.g. with an orienting margin, an orienting protrusion, an orienting constellation, or an orienting template) to a particular anatomical surface, and thus can be applied to the body to achieve a therapeutic result, without the assistance of an expert therapist. The device has the added benefit of being inexpensive to manufacture and easy to use compared to known acupressure devices.

In one embodiment, the device comprises a base sheet having a margin. The margin has at least a portion of its length shaped as an orienting margin, which corresponds to a shape on, or adjacent to, the selected skin surface portion. At least one protrusions is on the base sheet. Preferably, the orienting margin is suitable for positioning the protrusions of the device against the selected body surface for the application of acupressure to at least a portion of the selected body surface when the acupressure device is placed against the selected body surface. In another preferred embodiment, an adhesive layer is on a portion of the base sheet or protrusions, and the adhesive layer is suitable for attaching the device to the selected skin surface position.

In a further embodiment, the device of the present invention comprises a base sheet having one protrusion or a plurality of protrusions arranged in a constellation. The position of the one protrusion or the shape of the constellation corresponds to a shape on, or adjacent to, the selected skin surface portion when the base sheet is placed on the selected body surface. Thus, the one protrusion or the constellation can be used to orient the device on the skin surface. In a preferred embodiment, the shape of the constellation is suitable for positioning the protrusions of the device against the selected body surface for the application of acupressure to at least a portion of the selected body surface when the acupressure device is placed against the selected body surface. In another preferred embodiment, an adhesive layer is on a portion of the base sheet or protrusions, and the adhesive layer is suitable for attaching the device to the selected skin surface position.

In a further embodiment, the device of the present invention comprises a base sheet having orienting markings (e.g. printed, embossed, or varied on the device) that correspond to a shape on, or adjacent to, the selected skin surface portion when the base sheet is placed on the selected body surface. Thus, the markings can be used to orient the device on the skin surface. In a preferred embodiment, the shape of the markings is suitable for positioning the protrusions of the device against the selected body surface for the application of acupressure to at least a portion of the selected body surface when the acupressure device is placed against the selected body surface. In another preferred embodiment, an adhesive layer is on a portion of the base sheet or protrusions, and the adhesive layer is suitable for attaching the device to the selected skin surface position.

An object of the present invention is to provide a device that may be applied by any user with out any need for formal training in acupressure treatment or anatomy. This is accomplished by the device having an orienting margin, an orienting protrusion, an orienting constellation, or an orienting template which facilitates effective alignment and contact between the device and selected acupressure points. Such a device is preferably constructed with materials that are medically approved and hypoallergenic.

Another object of the present invention is to provide a device that is capable of adapting to a number of different treatments. This is accomplished by using any number of protrusion, in any number of different patterns, appropriate for any number of individual maladies and pains. The various different numbers of patterns or constellations are keyed to the corresponding orienting margins, which are then alignable to the appropriate anatomical landmark. This is to ensure that the proper treatment is applied to the proper skin area corresponding to the anatomical landmark.

The invention provides an acupressure device for use on a selected skin surface portion of a human body, the device comprising: a base sheet having a margin, wherein the margin has at least a portion shaped as an orienting margin which corresponds to a shape on or adjacent to the selected skin surface portion; at least one protrusion on the base sheet, and a fastener.

The invention also provides an acupressure device for use on a selected skin surface portion of a human body, the device comprising: a base sheet; a plurality of protrusions on the base sheet, wherein the plurality of protrusions is arranged in an orienting constellation having a shape that corresponds to a shape on or adjacent to the selected skin surface portion; and a fastener.

The invention also provides an acupressure device for use on a selected skin surface portion of a human body, the device comprising: a base sheet; one or more protrusions on the base sheet; and a fastener; wherein one or more protrusions is an orienting protrusion suitable for aligning the device to the selected skin surface portion.

The invention also provides an acupressure device for use on a selected skin surface portion of a human body, the device comprising: a base sheet; one or more protrusions on the base sheet; a fastener; and an orienting template on the base sheet suitable for aligning the device to the selected skin surface portion.

The invention also provides a device for treating premenstrual syndrome or menstrual cramps in a human, comprising: a base sheet having a margin, wherein the margin has at least a portion shaped as an orienting margin which corresponds to a shape on or adjacent to the triangular fossa, wherein said orienting margin positions the device to one or more therapy points on said triangular fossa; at least one protrusion on the base sheet, and a fastener.

The invention also provides a device for treating premenstrual syndrome or menstrual cramps in a human, comprising: a base sheet; a plurality of protrusions on the base sheet, wherein the plurality of protrusions is arranged in an orienting constellation having a shape that corresponds to a shape on or adjacent to the triangular fossa of a human; and a fastener.

The invention also provides a device for treating premenstrual syndrome or menstrual cramps in a human, comprising: a base sheet having an orienting template to position the device to one or more therapy points on the triangular fossa of the human; at least one protrusion on the base sheet, and a fastener.

The invention also provides a device for treating premenstrual syndrome or menstrual cramps in a human, comprising: a base sheet; at least one protrusion on the base sheet; and a fastener; wherein at least one protrusion is an orienting protrusion suitable for position the device to one or more therapy points on the triangular fossa of the human.

The invention also provides a device for treating smoking, drug or alcohol withdrawal in a human, comprising: a base sheet having a margin, wherein the margin has at least a portion shaped as an orienting margin which corresponds to a shape on or adjacent to the tragus or concha ridge of a human, wherein said orienting margin positions the device to one or more therapy points on said tragus or concha ridge; at least one protrusion on the base sheet, and a fastener.

The invention also provides a device for treating smoking, drug or alcohol withdrawal in a human, comprising: a base sheet; a plurality of protrusions on the base sheet, wherein the plurality of protrusions is arranged in an orienting constellation having a shape that corresponds to a shape on or adjacent to the tragus or concha ridge of a human; and a fastener.

The invention also provides a device for treating smoking, drug or alcohol withdrawal in a human, comprising: a base sheet having an orienting template to position the device to one or more therapy points on the tragus or concha ridge of a human; at least one protrusion on the base sheet, and a fastener.

The invention also provides a device for treating smoking, drug or alcohol withdrawal in a human, comprising: a base sheet; at least one protrusion on the base sheet; and a fastener; wherein at least one protrusion is an orienting protrusion suitable for position the device to one or more therapy points on the tragus or concha ridge of a human.

The invention also provides a device for treating headache or migraine headache in a human, comprising: a base sheet having a margin, wherein the margin has at least a portion shaped as an orienting margin which corresponds to a shape on or adjacent to the antitragus, wherein said orienting margin positions the device to one or more therapy points on said antitragus; at least one protrusion on the base sheet, and a fastener.

The invention also provides a device for treating headache or migraine headache in a human, comprising: a base sheet; a plurality of protrusions on the base sheet, wherein the plurality of protrusions is arranged in an orienting constellation having a shape that corresponds to a shape on or adjacent to the antitragus; and a fastener.

The invention also provides a device for treating headache or migraine headache in a human, comprising: a base sheet having an orienting template to position the device to one or more therapy points on the antitragus of a human; at least one protrusion on the base sheet, and a fastener.

The invention also provides a device for treating headache or migraine headache in a human, comprising: a base sheet; at least one protrusion on the base sheet; and a fastener; wherein at least one protrusion is an orienting protrusion suitable for position the device to one or more therapy points on the antitragus.

The invention also provides a device for treating lower back pain or sciatica, comprising: a base sheet having a margin, wherein the margin has at least a portion shaped as an orienting margin which corresponds to a shape on or adjacent to the cartilage ridge of a human ear, wherein said orienting margin positions the device to one or more therapy points on said cartilage ridge; at least one protrusion on the base sheet, and a fastener.

The invention also provides a device for treating lower back pain or sciatica in a human, comprising: a base sheet; a plurality of protrusions on the base sheet, wherein the plurality of protrusions is arranged in an orienting constellation having a shape that corresponds to a shape on or adjacent to the cartilage ridge of a human ear; and a fastener.

The invention also provides a device for treating lower back pain or sciatica, comprising: a base sheet having an orienting template to position the device to one or more therapy points on said cartilage ridge; at least one protrusion on the base sheet, and a fastener.

The invention also provides a device for treating lower back pain or sciatica in a human, comprising: a base sheet; at least one protrusion on the base sheet; and a fastener; wherein at least one protrusion is an orienting protrusion suitable for position the device to one or more therapy points on the cartilage ridge.

The invention also provides therapeutic methods for performing acupressure on a human in need of such therapy comprising applying a device of the invention to a preselected skin portion of the human. For example, the invention the following therapeutic methods which are provided to illustrate the methods of the invention, and are not intended to be limiting.

The invention provides a method for treating premenstrual syndrome or menstrual cramps in a human, comprising: applying an acupressure device to the human's triangular fossa, wherein the device comprises a base sheet having a margin, wherein the margin has at least a portion shaped as an orienting margin which corresponds to a shape on or adjacent to the triangular fossa, wherein said orienting margin positions the device to one or more therapy points on said triangular fossa; at least one protrusion on the base sheet, and a fastener.

The invention provides a method for treating premenstrual syndrome or menstrual cramps in a human, comprising: applying an acupressure device to the triangular fossa of the human, wherein the device comprises: a base sheet; a plurality of protrusions on the base sheet, wherein the plurality of protrusions is arranged in an orienting constellation having a shape that corresponds to a shape on or adjacent to the triangular fossa; and a fastener.

The invention provides a method for treating premenstrual syndrome or menstrual cramps in a human, comprising: applying an acupressure device to the human's triangular fossa, wherein the device comprises a base sheet having an orienting template to position the device to one or more therapy points on said triangular fossa; at least one protrusion on the base sheet, and a fastener.

The invention provides a method for treating premenstrual syndrome or menstrual cramps in a human, comprising: applying an acupressure device to the triangular fossa of the human, wherein the device comprises: a base sheet; at least one protrusion on the base sheet; and a fastener; wherein at least one protrusion is an orienting protrusion suitable for position the device to one or more therapy points on the triangular fossa.

The invention provides a method for treating smoking, drug or alcohol withdrawal in a human, comprising: applying an acupressure device to the human's tragus or concha ridge, wherein the device comprises a base sheet having a margin, wherein the margin has at least a portion shaped as an orienting margin which corresponds to a shape on or adjacent to the tragus or concha ridge, wherein said orienting margin positions the device to one or more therapy points on said tragus or concha ridge; at least one protrusion on the base sheet, and a fastener.

The invention provides a method for treating smoking, drug or alcohol withdrawal in a human, comprising: applying an acupressure device to the tragus or concha ridge of the human, wherein the device comprises: a base sheet; a plurality of protrusions on the base sheet, wherein the plurality of protrusions is arranged in an orienting constellation having a shape that corresponds to a shape on or adjacent to the tragus or concha ridge; and a fastener.

The invention provides a method for treating smoking, drug or alcohol withdrawal in a human, comprising: applying an acupressure device to the human's tragus or concha ridge, wherein the device comprises a base sheet having an orienting template to position the device to one or more therapy points on said tragus or concha ridge; at least one protrusion on the base sheet, and a fastener.

The invention provides a method for treating smoking, drug or alcohol withdrawal in a human, comprising: applying an acupressure device to the tragus or concha ridge of the human, wherein the device comprises: a base sheet; at least one protrusion on the base sheet; and a fastener; wherein at least one protrusion is an orienting protrusion suitable for position the device to one or more therapy points on the tragus or concha ridge.

The invention provides a method for treating headache or migraine headache in a human, comprising: applying an acupressure device to the human's antitragus, wherein the device comprises a base sheet having a margin, wherein the margin has at least a portion shaped as an orienting margin which corresponds to a shape on or adjacent to the antitragus, wherein said orienting margin positions the device to one or more therapy points on said antitragus; at least one protrusion on the base sheet, and a fastener.

The invention provides a method treating headache or migraine headache in a human, comprising: applying an acupressure device to the antitragus of the human, wherein the device comprises: a base sheet; a plurality of protrusions on the base sheet, wherein the plurality of protrusions is arranged in an orienting constellation having a shape that corresponds to a shape on or adjacent to the antitragus; and a fastener.

The invention provides a method for treating headache or migraine headache in a human, comprising: applying an acupressure device to the human's antitragus, wherein the device comprises a base sheet having an orienting template to position the device to one or more therapy points on said antitragus; at least one protrusion on the base sheet, and a fastener.

A method for treating headache or migraine headache in a human, comprising: applying an acupressure device to the antitragus of the human, wherein the device comprises: a base sheet; at least one protrusion on the base sheet; and a fastener; wherein at least one protrusion is an orienting protrusion suitable for position the device to one or more therapy points on the antitragus.

The invention provides a method for treating lower back pain or sciatica, comprising: applying an acupressure device on the human's cartilage ridge, wherein the device comprises a base sheet having a margin, wherein the margin has at least a portion shaped as an orienting margin which corresponds to a shape on or adjacent to the cartilage ridge, wherein said orienting margin positions the device to one or more therapy points on said cartilage ridge; and at least one protrusion on the base sheet, and a fastener.

The invention provides a method for treating lower back pain or sciatica in a human, comprising: applying an acupressure device on the cartilage ridge of the human, wherein the device comprises: a base sheet; a plurality of protrusions on the base sheet, wherein the plurality of protrusions is arranged in an orienting constellation having a shape that corresponds to a shape on or adjacent to the cartilage ridge; and a fastener.

The invention provides a method for treating lower back pain or sciatica, comprising: applying an acupressure device on the human's cartilage ridge, wherein the device comprises a base sheet having an orienting template to position the device to one or more therapy points on said cartilage ridge; at least one protrusion on the base sheet, and a fastener.

The invention provides a method a method for treating lower back pain or sciatica in a human, comprising: applying an acupressure device to the cartilage ridge of the human, wherein the device comprises: a base sheet; at least one protrusion on the base sheet; and a fastener; wherein at least one protrusion is an orienting protrusion suitable for position the device to one or more therapy points on the cartilage ridge.

These and other objects of the present invention and many of the attendant advantages of the present invention will be readily appreciated as the same become better understood by reference to the following detailed description when considered in connection with the accompanying drawings.

BRIEF DESCRIPTION OF THE DRAWINGS

FIG. 38B depicts a side plan view of a human ear, with a device of the present invention fastened to therapy points on the inferior concha, which can be used to treat asthma; FIG. 38A depicts the device used to treat asthma in FIG. 38B;

FIG. 39B depicts a side plan view of a human ear, with a device of the present invention fastened to therapy points on the anti helix tail and tragus, which can be used to treat motion and/or sea sickness; FIG. 39A and FIG. 39C depict the device used to treat motion and/or sea sickness in FIG. 39B;

FIG. 42B depicts a side plan view of a human ear with a device of the present invention partially fastened thereto.

DETAILED DESCRIPTION OF THE INVENTION

Figure 1:
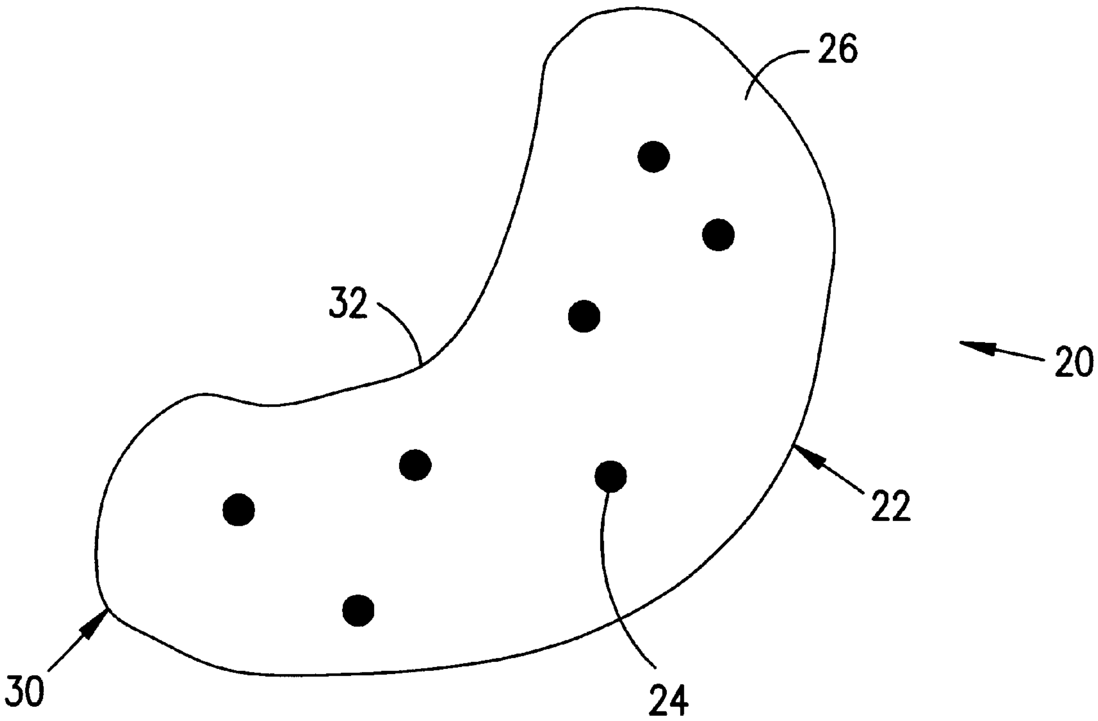
FIG. 1 is a bottom plan view of an embodiment of the present invention.
Figure 2:
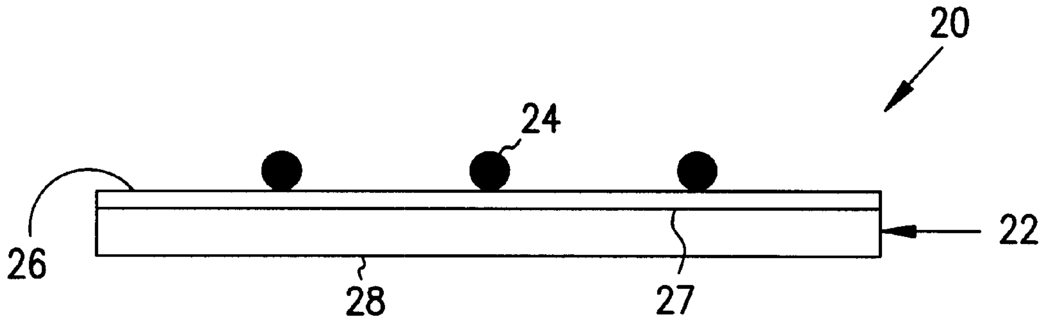
FIG. 2 is a side elevational view of the embodiment depicted in FIG. 1.

In reference to the various Figures, wherein like reference numbers refer to like components throughout the various Figures, there is disclosed an embodiment of the present invention is depicted in FIGS. 1 and 2 as an acupressure patch 20 comprising a base sheet 22 and at least one protrusion 24. Base sheet 22 includes an adhesive layer 26, a first side 27, an opposite outer surface 28 and a peripheral margin 30. Peripheral margin 30 includes an orienting margin 32 that is at least a portion of peripheral margin 30. Not depicted is a release film placed over first side 27 and at least one protrusion 24 at the time of manufacture. The purpose of a release film is to provide for convenient packaging and to prevent premature, inadvertent or undesired application of acupressure device 20. The types and uses of release films are well known in the art.

Base sheet 22 may be manufactured from a number of different materials ranging from a cloth to a film to any semi-ridgid or ridgid material. Various cloths useful as a base sheet include weaves made from synthetic or natural fibers, or a blend of both. Useful fibers include cotton, Dacron, polyester, and nylon. Alternatively, the base sheet may be a film made from natural or synthetic polymers and copolymers including cellulose, cellulose acetate, polyurethane, polyvinyl chloride, polyester, polypropylene, polyethylene, polytetrafluoroethylene, and various silicones and siloxane polymers. The film may be also be a foamed plastic. Alternatively, the base sheet may be comprised of a semi-ridgid or ridgid material, such as a metal or a metal alloy, e.g., a magnet. Useful metals include iron, stainless steel, nickel, copper, tin, zinc, platinum, titanium, gold and silver, and the various alloys attainable with these metals. A choice of metal or metal alloy may also depend on whether it is desired to include magnetic therapy using a magnetized metal or alloy with the use of the acupressure device. Preferably, the material used for base sheet 22 is of medical grade material desirable for its biocompatibility and is hypoallergenic.

As used herein, the term “protrusion” includes any type of object which projects from base sheet 22. A protrusion may be embedded in, affixed to, and/or molded from the base sheet 22. A protrusion, for example, may include, but is not limited to, a bead, a rounded mass, i.e., a nubbin or a disk; a nipple, a nodule, a lump, a projection, a knob, or a seed, or any combination thereof.

Figure 17:
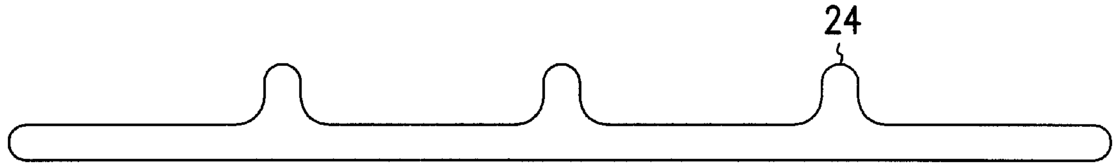
FIG. 17 depicts a side plan view of yet another further additional embodiment of the present invention.

FIG. 17 illustrates an additional embodiment of the present invention wherein the at least one protrusion 24 is molded from base sheet 22, as discussed above. For example, the protrusion may be created by deforming the surface of base sheet 22, such that protrusions are formed from the same material as the base sheet 22.

Figure 18:
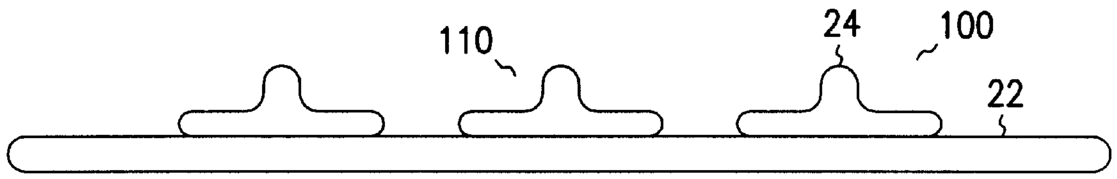
FIG. 18 depicts a side plan view of yet another further additional embodiment of the present invention.

FIG. 18 illustrates yet another additional embodiment, wherein at least one protrusion 24 is on base sheet 22, wherein protrusion 24 comprises disk 100, and wherein disk 100 further comprises at least one additional protrusion, e.g., a nipple 110, as discussed above.

Figure 19:
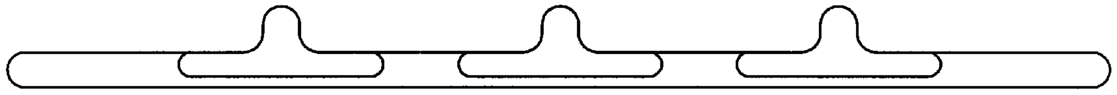
FIG. 19 depicts a side plan view of yet another further additional embodiment of the present invention.
Figure 20:
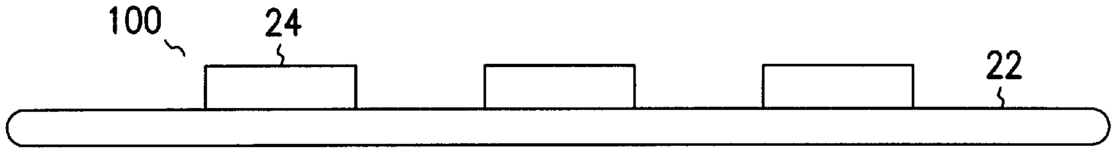
FIG. 20 depicts a side plan view of yet another further additional embodiment of the present invention.

FIG. 19 illustrates an additional embodiment of the present invention wherein the at least one protrusion 24 is embedded in base sheet 22 as discussed above. The one or more protrusion 24 may comprise a rounded mass, e.g., a disk or nubbin. Referring now to FIG. 20, an additional embodiment is illustrated, wherein protrusion 24 comprises a disk 100, which is affixed to base sheet 22.

The device may comprise any number of protrusions (e.g. beads) from one to greater than ten, or even twenty, arranged in a pattern intended for any number of possible treatment patterns, examples of which are to be explained below. Spacing of the protrusions is also dependent on the intended therapy and the site of on the skin the acupressure device is to be placed. The size of the bead may vary in diameter from less than about 0.5 mm to greater than about 5 mm.

The protrusion may be manufactured from a number of different materials including metals, metal alloys, various ceramics and glasses, hard rubbers, hard polymers, and organic materials. Useful metals include iron, stainless steel, nickel, copper, tin, zinc, platinum, titanium, gold and silver, and the various alloys attainable with these metals. A choice of metal or metal alloy may also depend on whether it is desired to include magnetic therapy using a magnetized metal or alloy with the use of the acupressure device.

As used herein, “fastener” includes magnetic fasteners (e.g. magnets), mechanical fasteners (e.g. a clamp, clip, wire, or a suction or spring loaded device), and chemical fasteners (e.g. a glue or adhesive).

Referring again to FIG. 1, wherein is depicted an adhesive layer 26. Adhesive layer 26 may be constructed from various adhesives in the form of pressure sensitive adhesives that are well known to the art. Choice of appropriate adhesive is guided by a desire to provide a medical grade, biocompatible, and hyperallergenic adhesive with good adhesive quality. Adhesive layer may also useful in adhering at least one protrusion 24 to base sheet 22.

Figure 3:
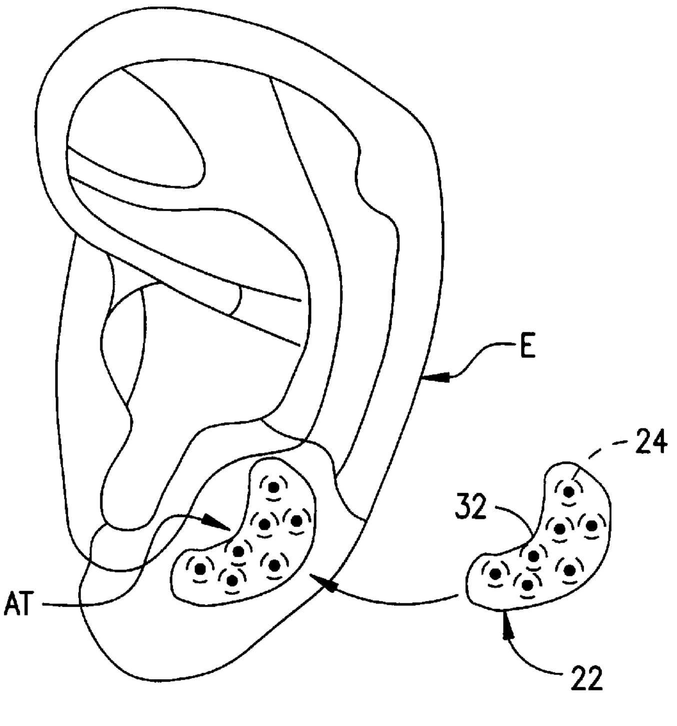
FIG. 3 is a top plan view of the embodiment depicted in FIG. 1 showing the relationship of the device to a specific anatomic landmark.

Peripheral margin 30 includes at least a portion of peripheral margin 30 as orienting margin 32. The present invention contemplates the use of various surface anatomic landmarks adjacent to known meridian points or zones, and homunculus representations to shape the orienting margin 32 to conform to the various surface anatomic landmarks of interest. By way of example, it is known that a person’s head is represented on a portion of the person’s pinna very near the anatomic landmark identified as the antitragus. The points of interest to the head correspond to therapy points used in acupressure to promote relief from headache occurring in those areas of the head so represented. This pattern of representation and the pattern’s spatial relationship to the antitragus is uniform from one person to the next. Therefore, orienting margin 32 may be shaped to contour the base of the antitragus, and at least one protrusion 24 may be positioned on base sheet 22 relative to orienting margin 32 to correspond to at least one therapy point in the vicinity of the antitragus. Just such an example using known therapy points is depicted in FIG. 3.

In addition, one untrained in the art of acupressure may successfully adiminster acupressure therapy using a device of the invention that comprises one a plurality of protrusions, which are arranged in a pre-determined pattern, i.e. a constellation. As with the orienting margin discussed above, a constellation, by the nature of its shape, can form an orienting constelation that allows the user to position the device over therapy points on the anatomic area such that it will provide acupressure to at least a portion of the selected body surface. The orienting constellation may be shaped so that the present device may be positioned for use on or about the ear, hands, nose or feet. On or about the ear, for example, a constellation may position the device to the tragus, antitragus, uterine point, shen men, antidepressent areas, helix, antihelix, triangular or schaphoid fossa, the cartilage ridge or other points of the pinna, or concha.

A given constellation may also allow the device to conform to additional therapy points on the human body including, for example, on the hand, palm or fingers, for the treatment of anterior portions of the head, face, neck, upper chest, back of head or spine. Additional sites used in acupressure will be known to one of skill in the art.

Figure 34A:
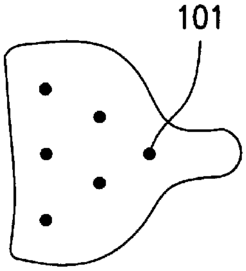
FIG. 34A depicts the device used to treat smoking, drug or alcohol withdrawal in FIG. 34B.
Figure 34B:
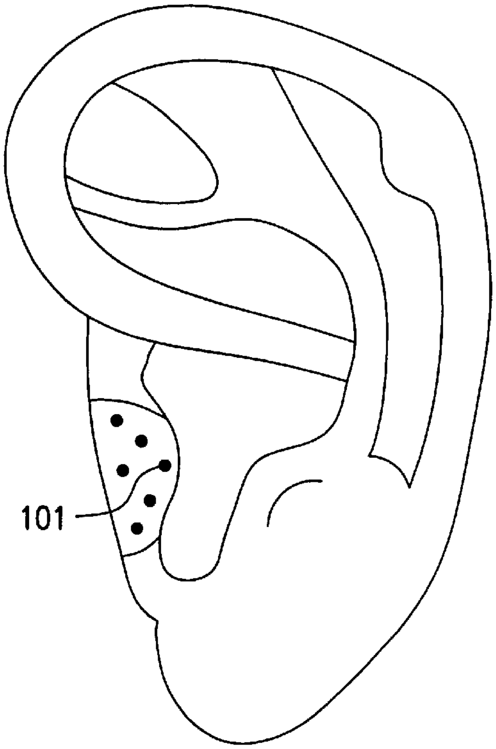
FIG. 34B depicts a side plan view of a human ear, with a device of the present invention fastened to therapy points on the tragus, which can be used to treat smoking, drug or alcohol withdrawal.

A device of the invention can also comprise a single protrusion that is positioned to allow a user to position the device over therapy points on the anatomic area such that it will provide acupressure to at least a portion of the selected body surface. This orienting protrusion can function alone to orient the device, or the device can comprise an orienting protrusion in combination with an orienting margin and/or an orienting constellation. The orienting protrusion may orient the device for use on a preselected surface of the ear, hands, nose, feet, or other part of the body. For example, the orienting protrusion may orient the device to therapy points on the human body including, for example, on the hand, palm or fingers, for the treatment of anterior portions of the head, face, neck, upper chest, back of head or spine. Additional sites used in acupressure will be known to one of skill in the art. For example, as illustrated in FIGS. 34A and 34B, a device of the invention can be aligned on the tragus, using a single orienting protrusion 101 that is aligned with the tip of the tragus.

The orienting margin, orienting constellation, orienting protrusion, or orienting template is arranged in such a manner as to allow the user to apply acupressure to therapy points for the treatment of general headaches, migraine headaches, premenstrual syndrome, menstrual cramps, depression, impotency, libido, appetite suppression, low back pain, sciatica, fatigue, chronic fatigue, insomnia, jet lag, stress, anxiety, shoulder pain, neck pain, temporomandibular joint dysfunction (TMJ), jaw pain, smoking, drug or alcohol withdrawal, alcoholism, sinusitus, allergies, asthma, motion and sea sickness, stomach ache, indigestion, heartburn, acid reflux, or nausea. Additional indications will be known to one of skill in the art.

Figure 4:
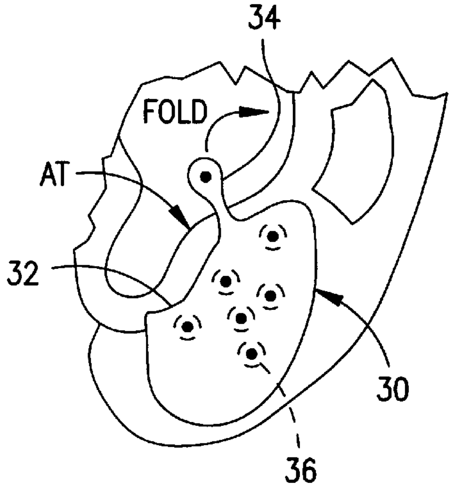
FIG. 4 is a top plan view of an alternative embodiment of the present invention shown in relationship to a specific anatomic landmark.
Figure 5:
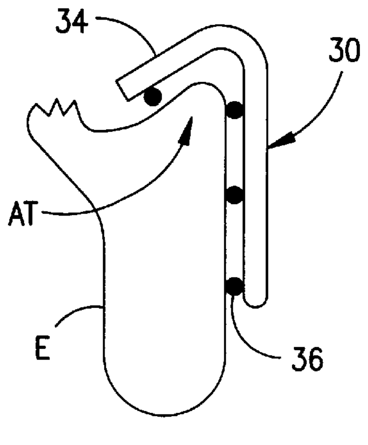
FIG. 5 is a side elevational view of the embodiment depicted in FIG. 4 shown in position in relationship to a specific anatomic landmark.

FIG. 4 depicts a variation of the embodiment of the present invention wherein orienting margin 32 extends an accessory lobe 34 to an adjacent therapy point. In this example, accessory lobe 34 is extended to the therapy point on the inner surface of the pinna representing area subcortex by folding accessory lobe 34 over the rim the anithelix of the pinna to reach SC. FIG. 5 shows a side elevational view depicting how this positioning is accomplished.

Figure 6:
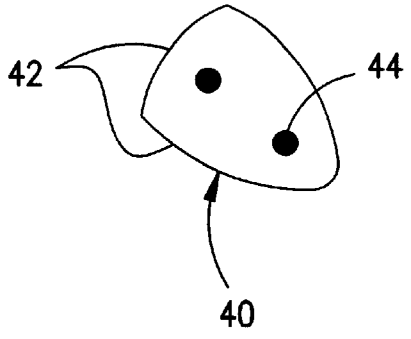
FIG. 6 is a bottom plan view of an additional alternative embodiment of the present invention.
Figure 7:
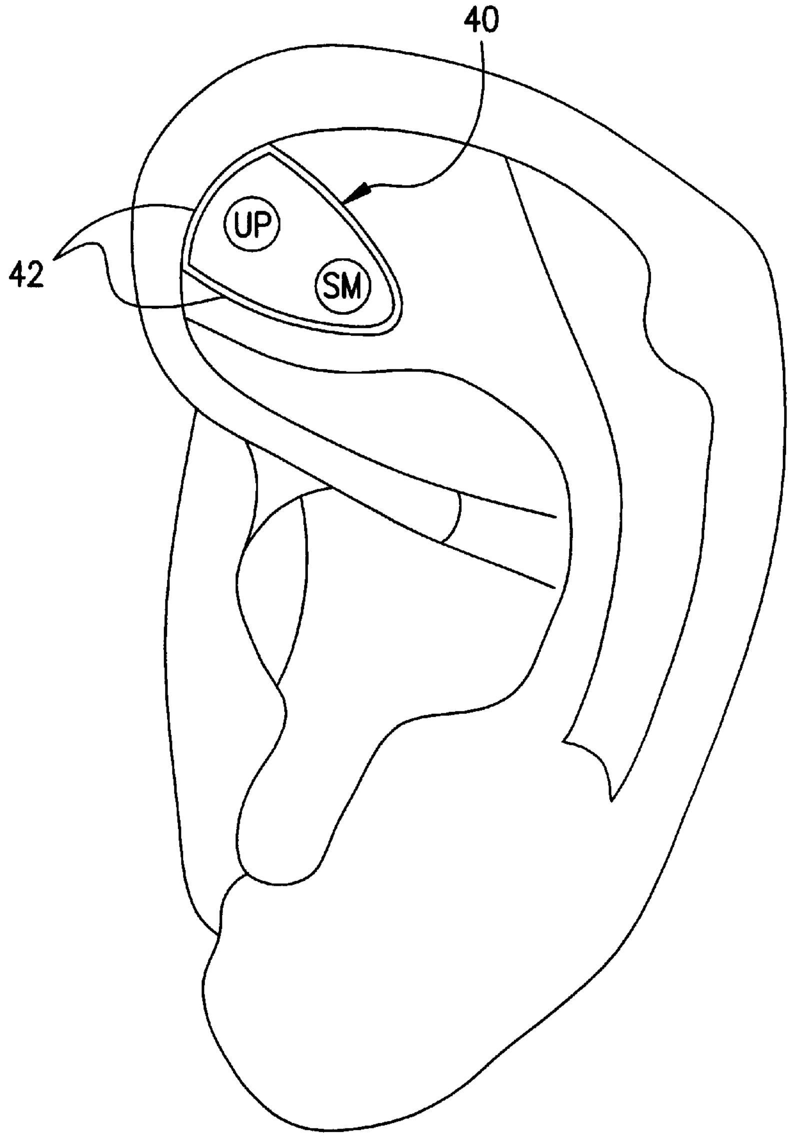
FIG. 7 is a top plan view of the embodiment depicted in FIG. 6 shown in relationship to a specific anatomic landmark.

A majority of the surface of a person's pinna represents the body in the form of a homunculus. As noted above, various areas of a person's ipsilateral skull area represented by therapy points proximate the antitragus. FIG. 6 discloses an acupressure device 40 having an orienting margin 42 and at least one bead 44. In FIG. 7, there is shown the representative points of the body for the uterus point UP and the shen men SM which are found near the inner margin of the triangular fossa. Acupressure device 40 is positioned with orienting margin 42 adjacent the inner margin of the triangular fossa to position protrusions 44 over the therapy points UP and SM.

Figure 9:
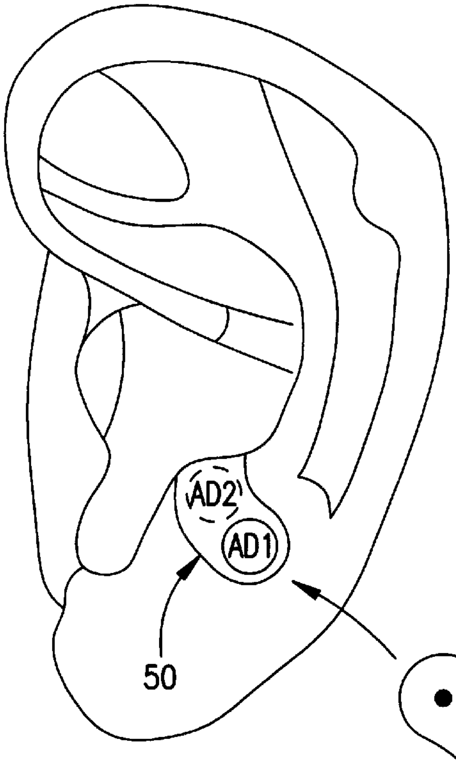
FIG. 9 is a partial plan view of the embodiment depicted in FIG. 8 shown wrapping over a specific anatomic landmark.
Figure 8:
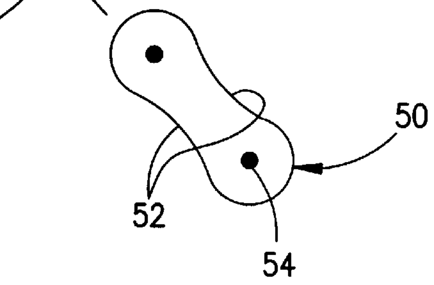
FIG. 8 is a bottom plan view of another additional alternative embodiment of the present invention.
Figure 10:
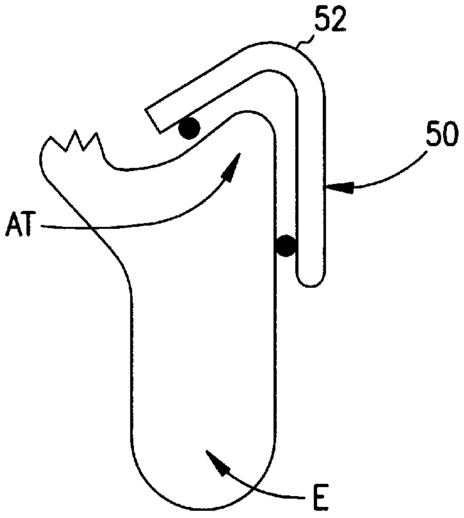
FIG. 10 is a side elevational view of the embodiment of FIG. 8 shown in relationship to a specific anatomic landmark.

Another example is depicted in FIGS. 8–10 disclosing an acupressure device 50 having an orienting margin 52 in the shape of a wasp waste and at least one bead 54. Represented on the surface of a person's pinna are two antidepressant areas AD1 and AD2. These two areas are opposite each other over the rim of the antihelix proximate the point where the antihelix meets the edge of the antitragus. Orienting margin 52 fits within the hollow found at the junction between the antihelix and antitragus thus positioning acupressure device 50 and its associated protrusions 54 over therapy points 1 and 2.

Additional embodiments of the invention are illustrated in FIGS. 21–44.

Figure 21:
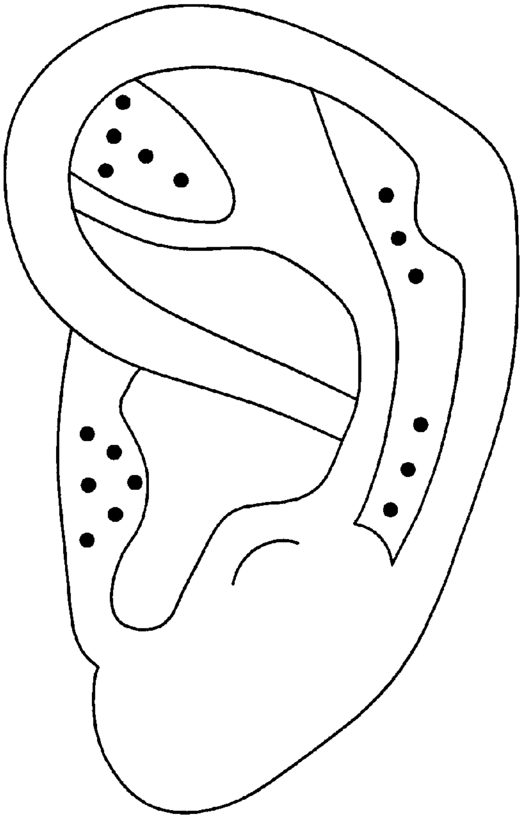
FIG. 21 is a top plan view of an alternative embodiment of the present invention shown in relationship to a specific anatomic landmark.
Figure 22:
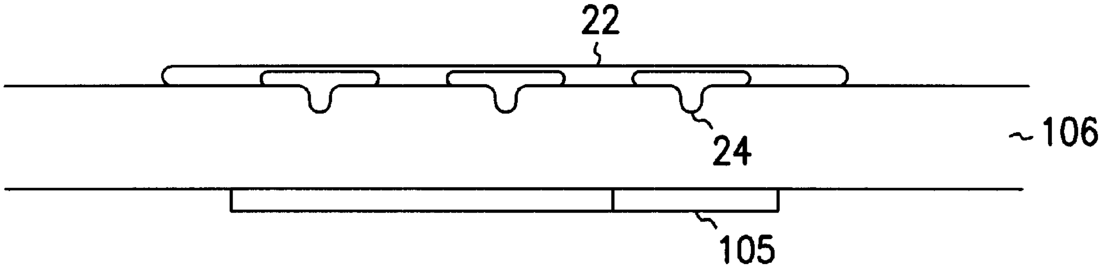
FIG. 22 depicts a side plan view of yet another further additional embodiment of the present invention.

FIG. 21 is a top plan view of three alternative embodiments of the present invention shown in relationship to a specific anatomic landmark on the human ear;

FIG. 22 depicts a magnetic base sheet 22 comprising protrusions 24 held in place on a selected skin surface of the human body 106 with a magnetic fastener 105.

Figure 23A:
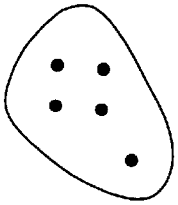
FIG. 23A depicts the device used to treat premenstrual syndrome and/or menstrual cramps in FIG. 23B.
Figure 23B:
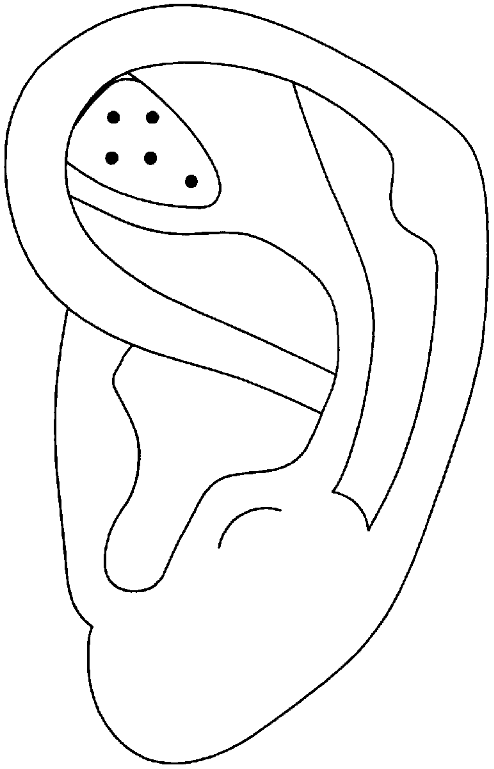
FIG. 23B depicts a side plan view of a human ear, with a device of the invention fastened to therapy points on the triangular fossa, which can be used to treat premenstrual syndrome and/or menstrual cramps.

FIG. 23B depicts a side plan view of a human ear, with a device of the invention fastened to therapy points on the triangular fossa, which can be used to treat premenstrual syndrome and/or menstrual cramps; FIG. 23A depicts the device used to treat premenstrual syndrome and/or menstrual cramps in FIG. 23B.

Figure 24B:
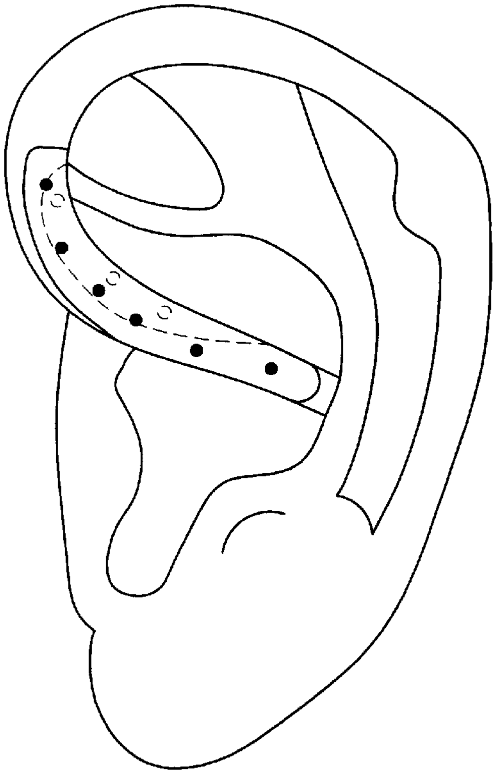
FIG. 24B depicts a side plan view of a human ear, with a device of the invention fastened to therapy points on the helix root, which can be used to treat impotency or libido.
Figure 24A:
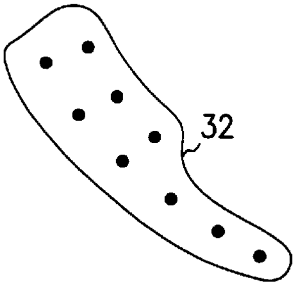
FIG. 24A depicts the device used to treat impotency or libido in FIG. 24B.

FIG. 24B depicts a side plan view of a human ear, with a device of the invention fastened to therapy points on the helix root, which can be used to treat impotency or libido; FIG. 24A depicts the device used to treat impotency or libido with orienting margin 32.

Figure 25D:
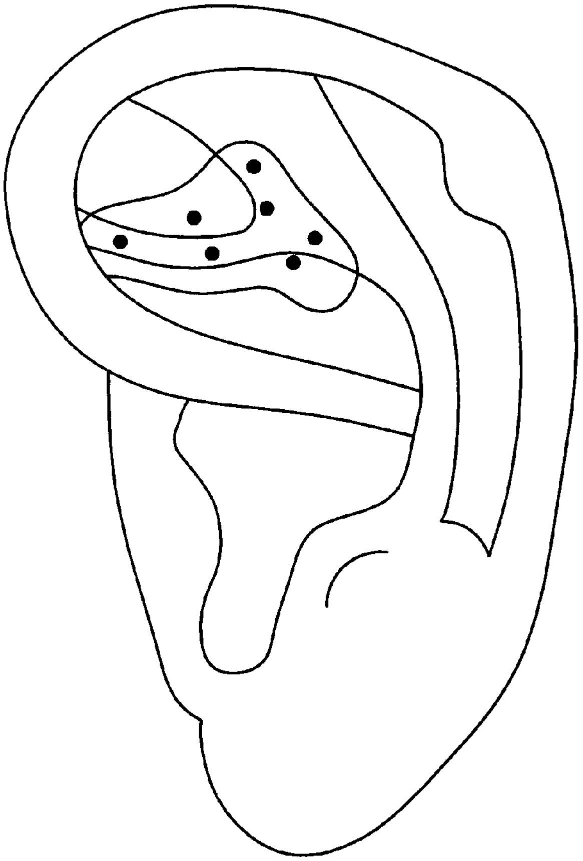
FIG. 25D depicts a side plan view of a human ear, with a device of the invention fastened to therapy points on the anti helix, which can be used to treat lower back pain and/or sciatica.
Figure 25A:
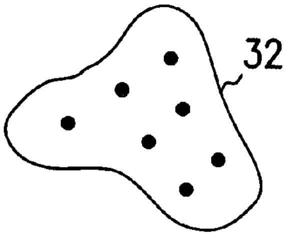
FIG. 25A depicts the device used to treat lower back pain and/or sciatica in FIG. 25D; additional embodiments of the device used to treat lower back pain and/or sciatica are depicted in FIGS. 25B and 25C.
Figure 25C:
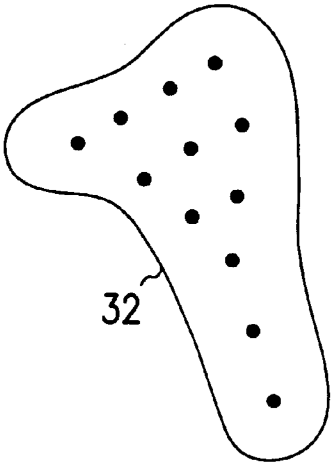
Figure 25B:
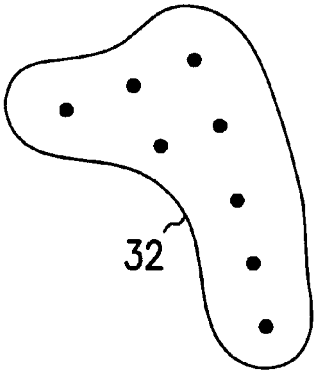

FIG. 25D depicts a side plan view of a human ear, with a device of the invention fastened to therapy points on the anti helix, which can be used to treat lower back pain and/or sciatica; FIG. 25A depicts the device used to treat lower back pain and/or sciatica with orienting margin 32; additional embodiments of the device used to treat lower back pain and/or sciatica are depicted in FIGS. 25B and 25C, with orienting margins 32.

Figure 26A:
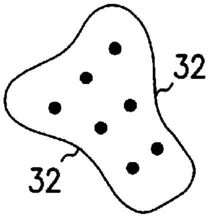
FIG. 26A depicts the device used to treat lower back pain and/or sciatica in FIG. 26B.
Figure 26B:
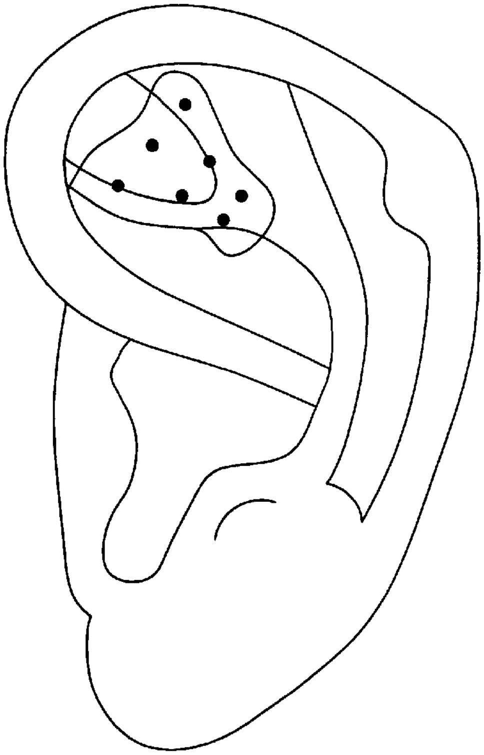
FIG. 26B depicts a side plan view of a human ear, with a device of the invention fastened to therapy points on the anti helix and triangular fossa, which can be used to treat lower back pain and/or sciatica.

FIG. 26B depicts a side plan view of a human ear, with a device of the invention fastened to therapy points on the anti helix and triangular fossa, which can be used to treat lower back pain and/or sciatica; FIG. 26A depicts the device used to treat lower back pain and/or sciatica, with orienting margins 32.

Figure 27B:
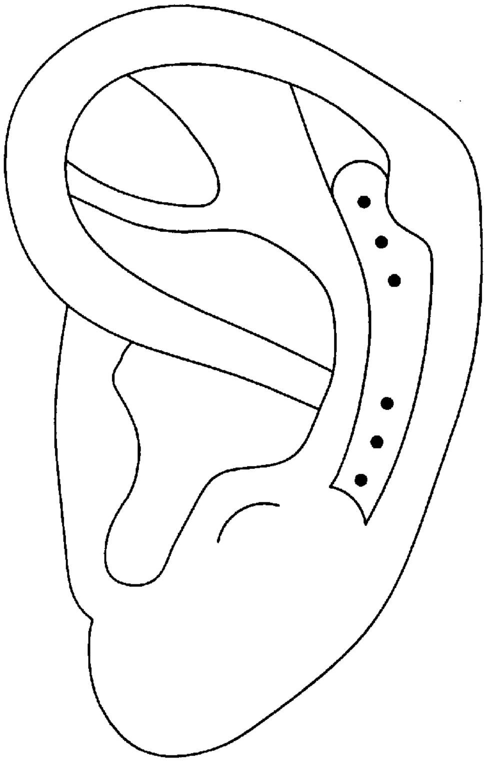
FIG. 27B depicts a side plan view of a human ear, with a device of the invention fastened to therapy points on the scaphiod fossa, which can be used to treat insomnia and/or jet lag.
Figure 27A:
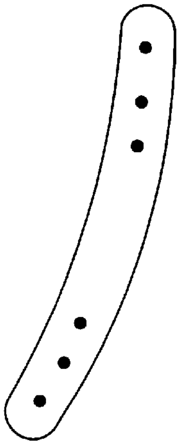
FIG. 27A depicts the device used to treat insomnia and/or jet lag in FIG. 27A.

FIG. 27B depicts a side plan view of a human ear, with a device of the invention fastened to therapy points on the scaphiod fossa, which can be used to treat insomnia and/or jet lag; FIG. 27A depicts the device used to treat insomnia and/or jet lag in FIG. 27A.

Figure 28A:
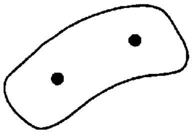
FIG. 28A depicts the device used to treat stress and/or anxiety in FIG. 28B.
Figure 28B:
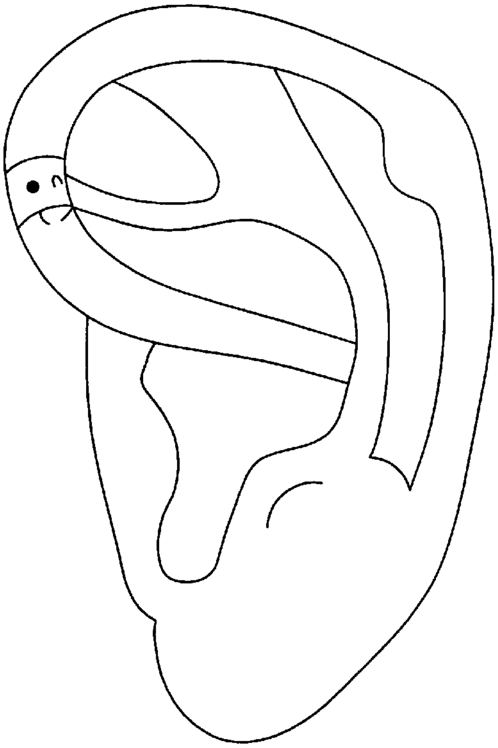
FIG. 28B depicts a side plan view of a human ear, with a device of the invention fastened to therapy points on the helix, which can be used to treat stress and/or anxiety.

FIG. 28B depicts a side plan view of a human ear, with a device of the invention fastened to therapy points on the helix, which can be used to treat stress and/or anxiety; FIG. 28A depicts the device used to treat stress and/or anxiety in FIG. 28B.

Figure 29A:
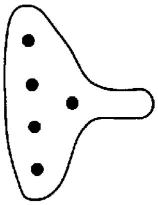
FIG. 29A depicts the device used to treat fatigue in FIG. 29B.
Figure 29B:
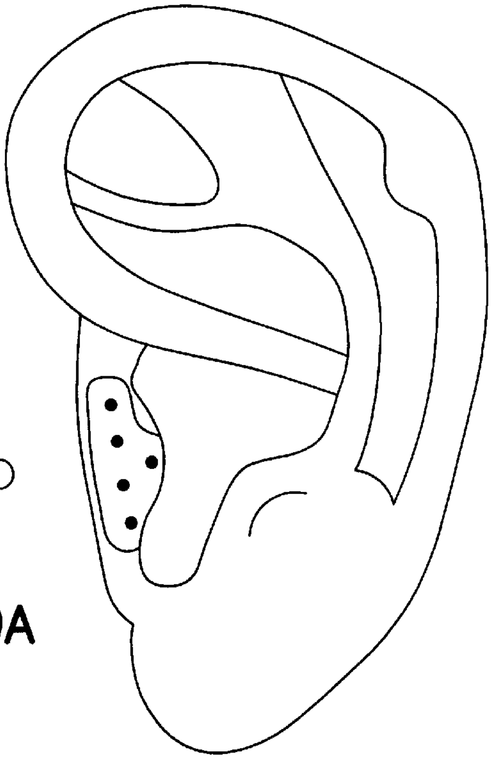
FIG. 29B depicts a side plan view of a human ear, with a device of the present invention fastened to therapy points on the tragus, which can be used to treat fatigue.

FIG. 29B depicts a side plan view of a human ear, with a device of the present invention fastened to therapy points on the tragus, which can be used to treat fatigue; FIG. 29A depicts the device used to treat fatigue in FIG. 29B.

Figure 30A:
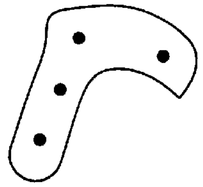
FIG. 30A depicts the device used to treat the shoulder in FIG. 30B.
Figure 30B:
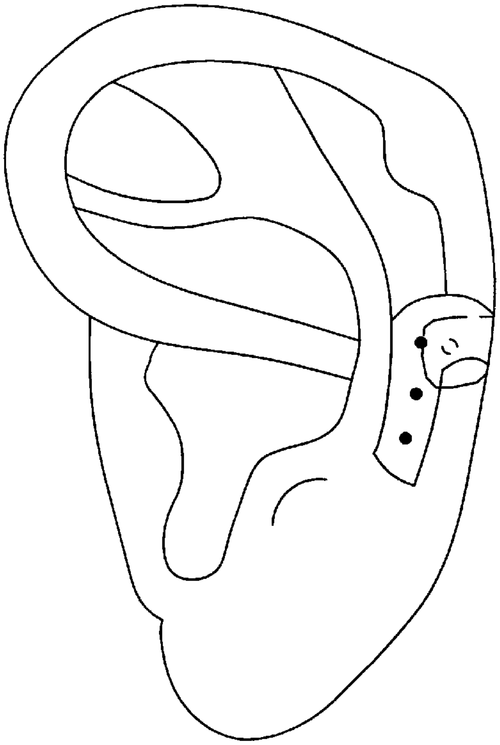
FIG. 30B depicts a side plan view of a human ear, with a device of the present invention fastened to therapy points on the lower scaphoid, which can be used to treat ailments of the shoulder.
Figure 31B:
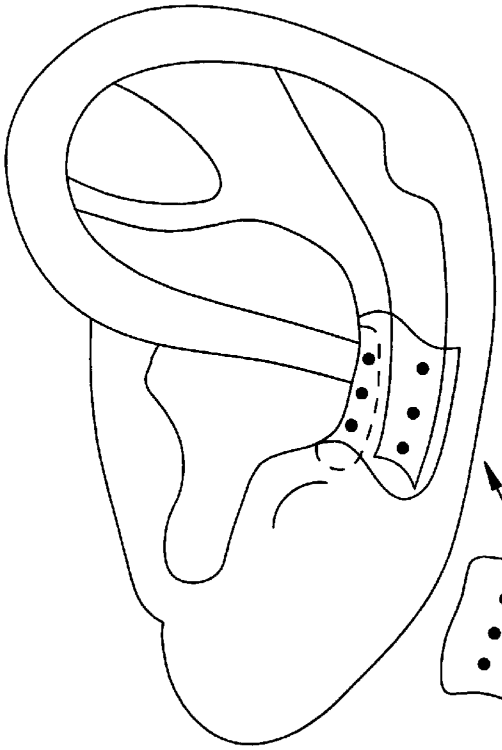
FIG. 31B depicts a side plan view of a human ear, with a device of the present invention fastened to therapy points on the anti helix tail and lower scaphoid fossa, which can be used to treat neck pain and/or shoulder pain.
Figure 31A:
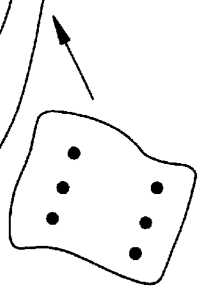
FIG. 31A depicts the device used to treat neck pain and/or shoulder pain in FIG. 31B.
Figure 32A:
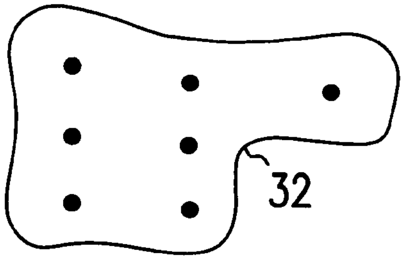
FIG. 32A depicts the device used to treat neck and shoulder pain in FIG. 32B.
Figure 32B:
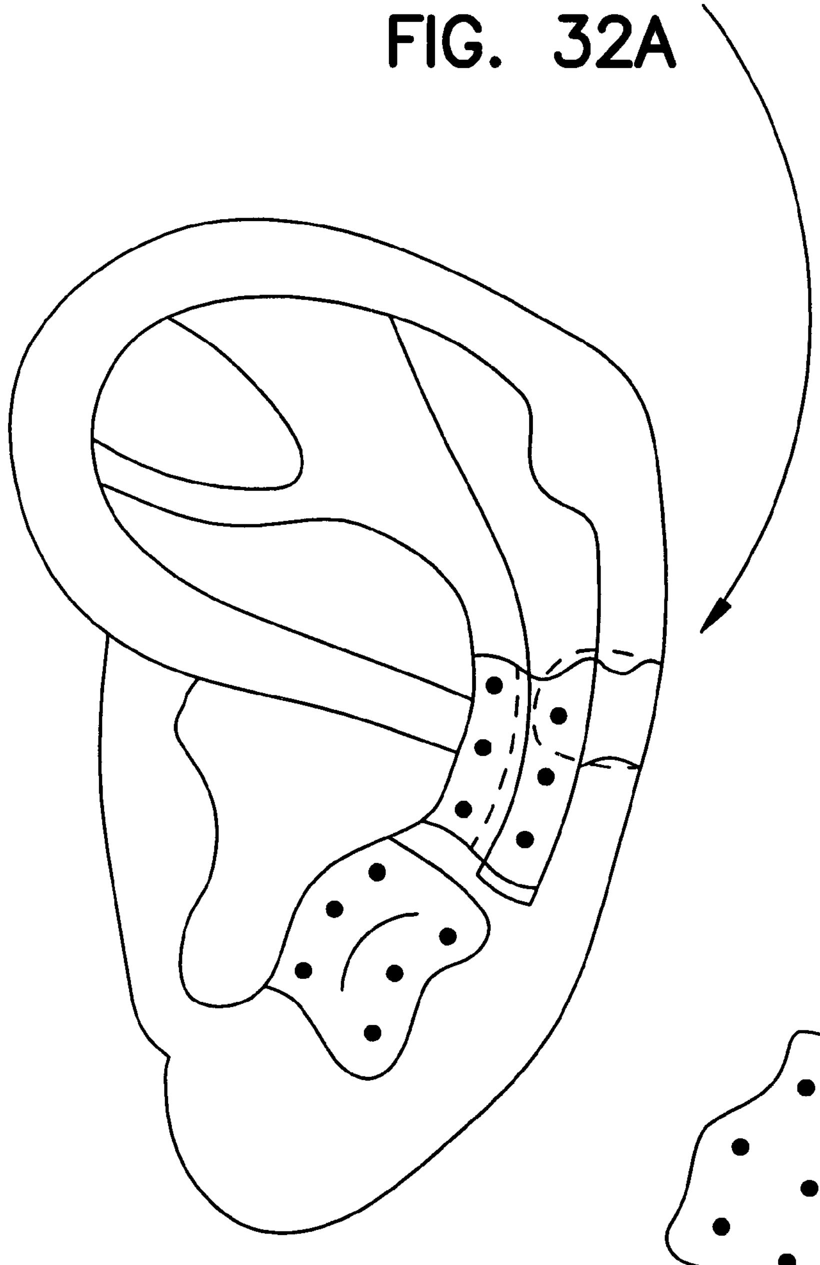
FIG. 32B depicts a side plan view of a human ear, with a device of the present invention fastened to therapy points on the anti tragus, antihelix tail, or scophoid fossa, which can be used to treat neck and shoulder pain.
Figure 32C:
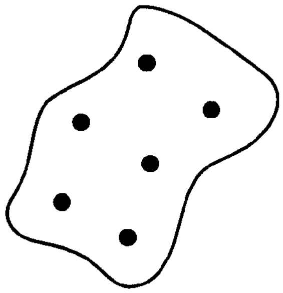
FIG. 32C depicts an additional embodiment of the device which may be used to treat neck and shoulder pain.
Figure 33B:
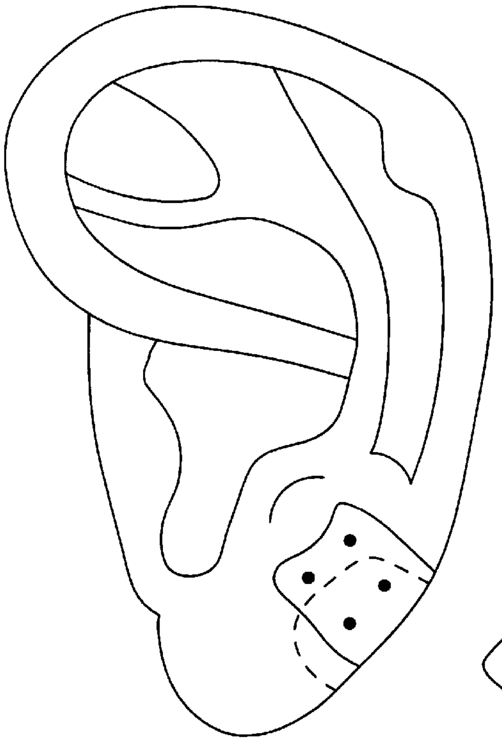
FIG. 33B depicts a side plan view of a human ear, with a device of the present invention fastened to therapy points on the upper posterior ear lobe, which can be used to treat temporomandibular joint dysfunction (TMJ)
Figure 33A:
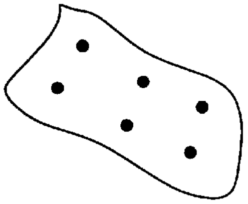
FIG. 33A depicts the device used to treat temporomandibular joint dysfunction (TMJ) in FIG. 33B.

FIG. 30B depicts a side plan view of a human ear, with a device of the present invention fastened to therapy points on the lower scaphoid, which can be used to treat ailments of the shoulder; FIG. 30A depicts the device used to treat the shoulder in FIG. 30B;

FIG. 31B depicts a side plan view of a human ear, with a device of the present invention fastened to therapy points on the anti helix tail and lower scaphoid fossa, which can be used to treat neck pain and/or shoulder pain; FIG. 31A depicts the device used to treat neck pain and/or shoulder pain in FIG. 31B;

FIG. 32B depicts a side plan view of a human ear, with a device of the present invention fastened to therapy points on the anti tragus, antihelix tail, or scophoid fossa, which can be used to treat neck and shoulder pain; FIG. 32A depicts the device with orienting margin 32 used to treat neck and shoulder pain in FIG. 32B; FIG. 32C depicts an additional embodiment of the device which may be used to treat neck and shoulder pain;

FIG. 33B depicts a side plan view of a human ear, with a device of the present invention fastened to therapy points on the upper posterior ear lobe, which can be used to treat temporomandibular joint dysfunction (TMJ); FIG. 33A depicts the device used to treat temporomandibular joint dysfunction (TMJ) in FIG. 33B;

FIG. 34B depicts a side plan view of a human ear, with a device of the present invention with orienting protrusion 101 fastened to therapy points on the tragus, which can be used to treat smoking, drug or alcohol withdrawal; FIG. 34A depicts the device used to treat smoking, drug or alcohol withdrawal in FIG. 34B, with orienting protrusion 101.

Figure 35C:
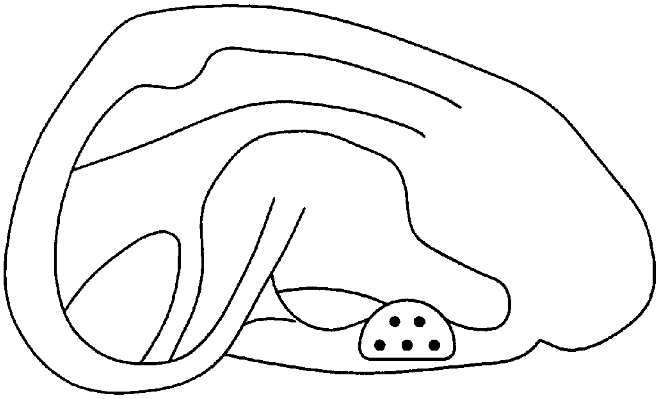
FIG. 35B, and FIG. 35C depict side plan views of a human ear, with a device of the present invention fastened to therapy points on the tragus, which can be used to treat smoking, drug or alcohol withdrawal, or to promote weight loss.
Figure 35B:
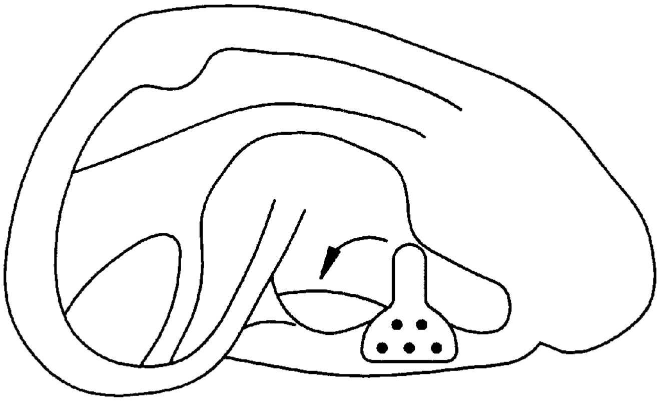
Figure 35A:
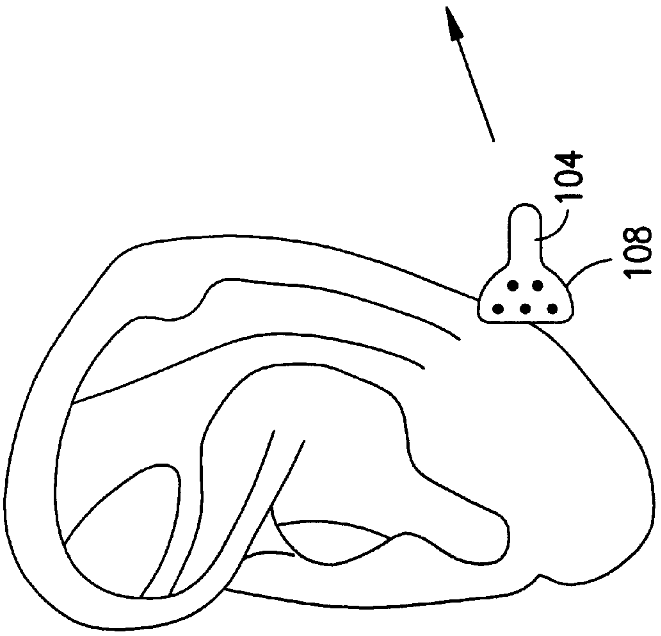
FIG. 35A depicts a human ear, with a device of the present invention having an orienting margin suitable for orienting the device to the tragus.

FIG. 35A depicts a human ear, with a device of the present invention 104 having an orienting margin 108 suitable for orienting the device to the tragus. FIG. 35B, and FIG. 35C depict side plan views of a human ear, with a device of the present invention fastened to therapy points on the tragus, which can be used to treat smoking, drug or alcohol withdrawal, or to promote weight loss.

Figure 36A:
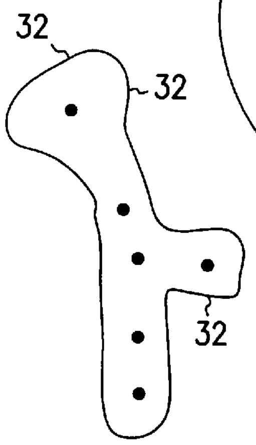
FIG. 36A depicts the device used to treat smoking, drug and/or alcohol addiction in FIG. 36B.
Figure 36B:
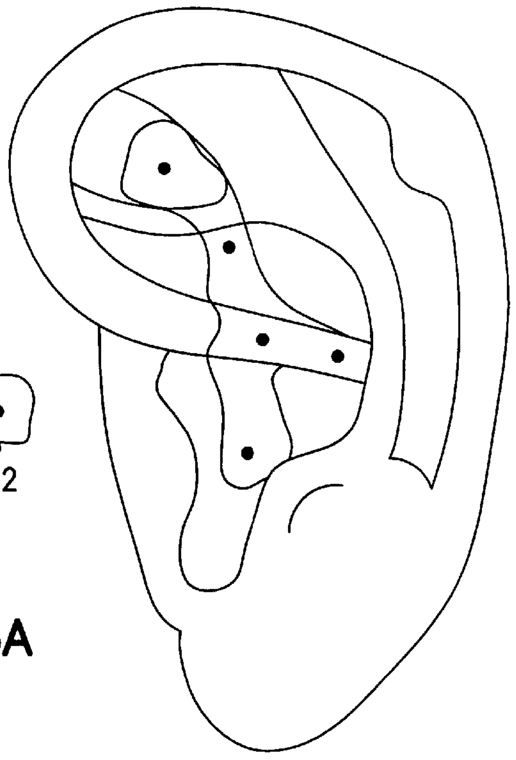
FIG. 36B depicts a side plan view of a human ear, with a device of the present invention fastened to therapy points on the triangular fossa, superior and inferior concha, and concha ridge, which can be used to treat smoking, drug and/or alcohol addiction.

FIG. 36B depicts a side plan view of a human ear, with a device of the present invention fastened to therapy points on the triangular fossa, superior and inferior concha, and concha ridge, which can be used to treat smoking, drug and/or alcohol addiction; FIG. 36A depicts the device used to treat smoking, drug and/or alcohol addiction in FIG. 36B, with orienting margins 32.

Figure 37A:
FIG. 37A depicts the device used to treat allergies in FIG. 37B.
Figure 37B:
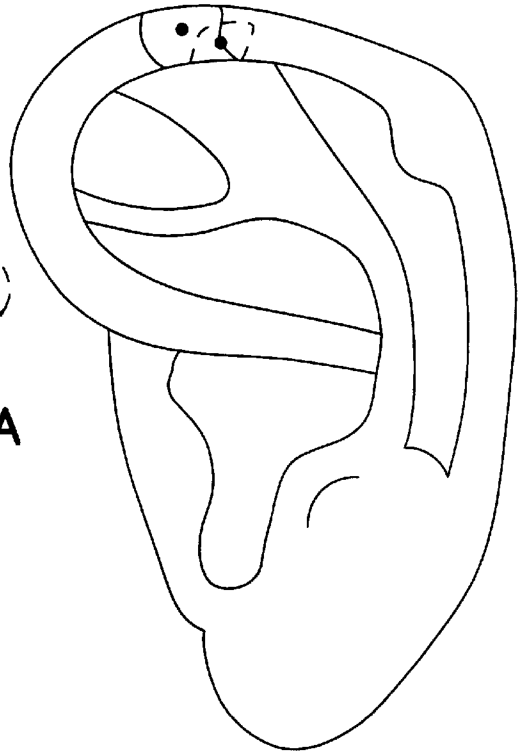
FIG. 37B depicts a side plan view of a human ear, with a device of the present invention fastened to therapy points on the superior helix, which can be used to treat allergies.

FIG. 37B depicts a side plan view of a human ear, with a device of the present invention fastened to therapy points on the superior helix, which can be used to treat allergies; FIG. 37A depicts the device used to treat allergies in FIG. 37B.

FIG. 38B depicts a side plan view of a human ear, with a device of the present invention fastened to therapy points on the inferior concha, which can be used to treat asthma; FIG. 38A depicts the device used to treat asthma in FIG. 38B.

Figure 40B:
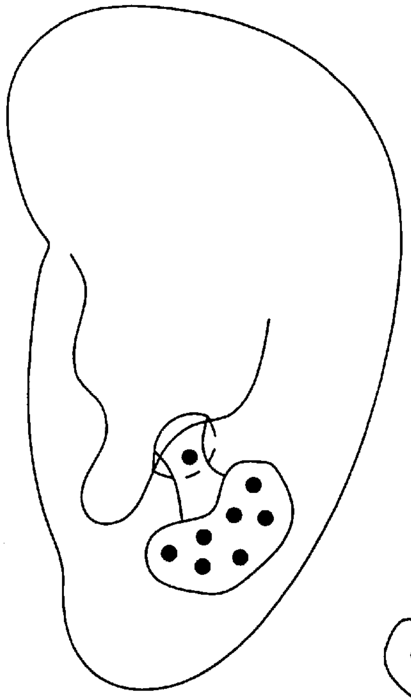
FIG. 40B depicts a side plan view of a human ear, with a device of the present invention fastened to therapy points on the upper lobe and anti tragus, which can be used to treat migraine headache.
Figure 40A:
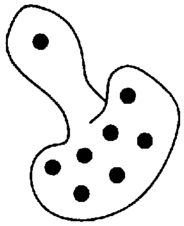
FIG. 40A depicts the device used to treat migraine headache in FIG. 40B.

FIG. 39B depicts a side plan view of a human ear, with a device of the present invention fastened to therapy points on the anti helix tail and tragus, which can be used to treat motion and/or sea sickness; FIG. 39A and FIG. 39C depict the device used to treat motion and/or sea sickness in FIG. 39B;

FIG. 40B depicts a side plan view of a human ear, with a device of the present invention fastened to therapy points on the upper lobe and anti tragus, which can be used to treat migraine headache; and FIG. 40A depicts the device used to treat migraine headache in FIG. 40B.

Figure 41:
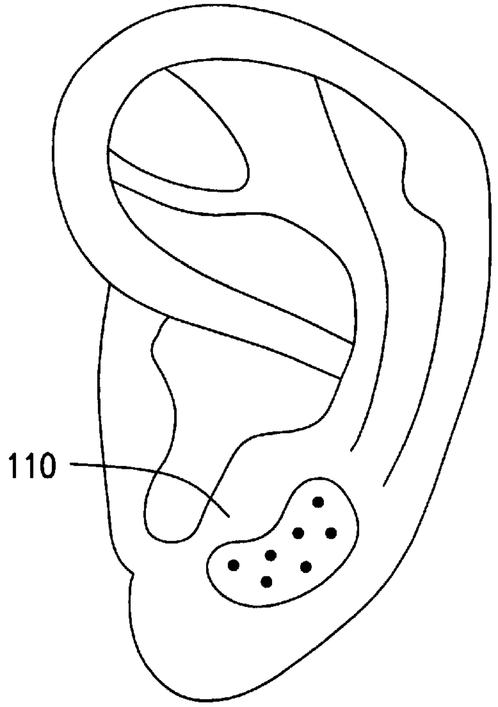
FIG. 41 depicts a side plan view of a human ear, with a device of the present invention fastened to therapy points positioned near the antitragus 110, which can be used to treat headache or migraine headache.
Figure 42A:
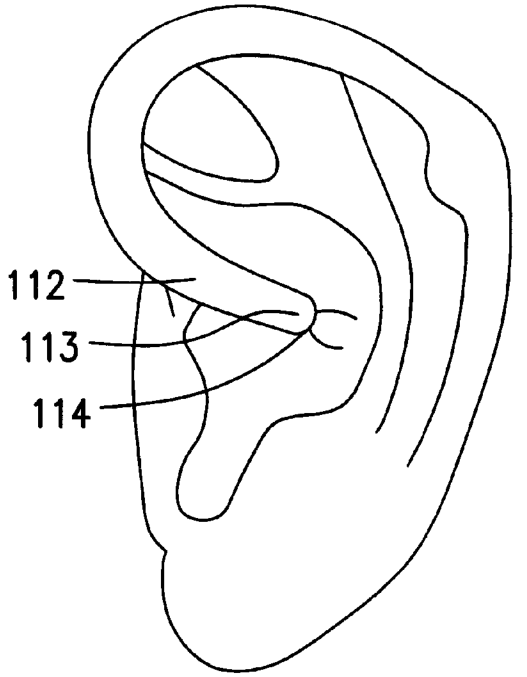
FIG. 42A depicts a side plan view of a human ear.
Figure 42B:
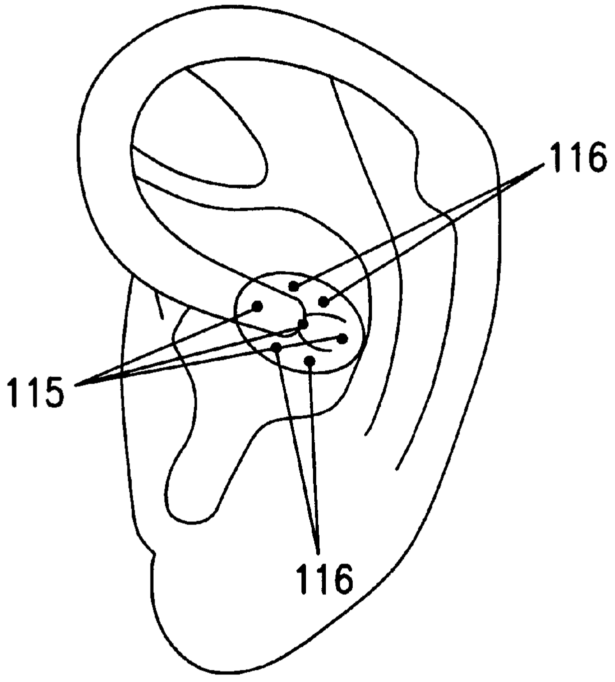
FIG. 42B depicts a side plan view of a human ear with a device of the present invention fastened to therapy points on or near the helical ridge, which can be used to induce appetight suppression or to promote weight loss.

FIG. 41 depicts a side plan view of a human ear, with a device of the present invention fastened to therapy points positioned near the antitragus 110, which can be used to treat headache or migraine headache;

FIG. 42A depicts a side plan view of a human ear, and FIG. 42B depicts a side plan view of a human ear with helical ridge 112, end of ridge 113 and indentation is ridge 114; FIG. 42B depicts a device of the present invention, having orienting constellation 115 over the ridge, and orienting constellation 116 adjacent to the ridge, fastened to therapy points on or near the helical ridge, which can be used to induce appetight suppression or to promote weight loss.

Figure 43C:
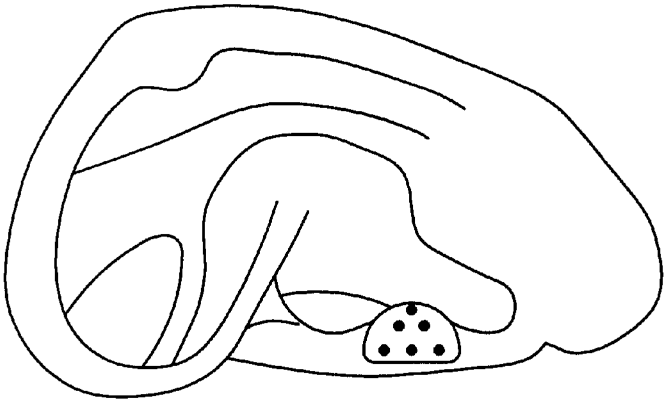
FIG. 43C depicts a side plan view of a human ear, with a device of the invention fastened to therapy points on the tragus, which can be used to treat smoking, drug or alcohol withdrawal, or to promote weight loss.
Figure 43B:
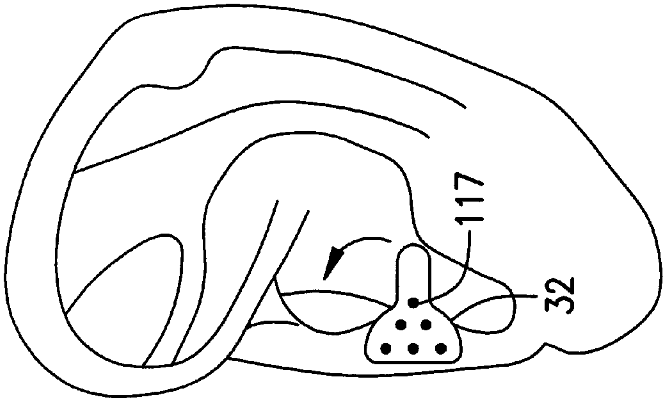
FIG. 43A depicts a side plan view of a human ear, and a device of the invention.
Figure 43A:
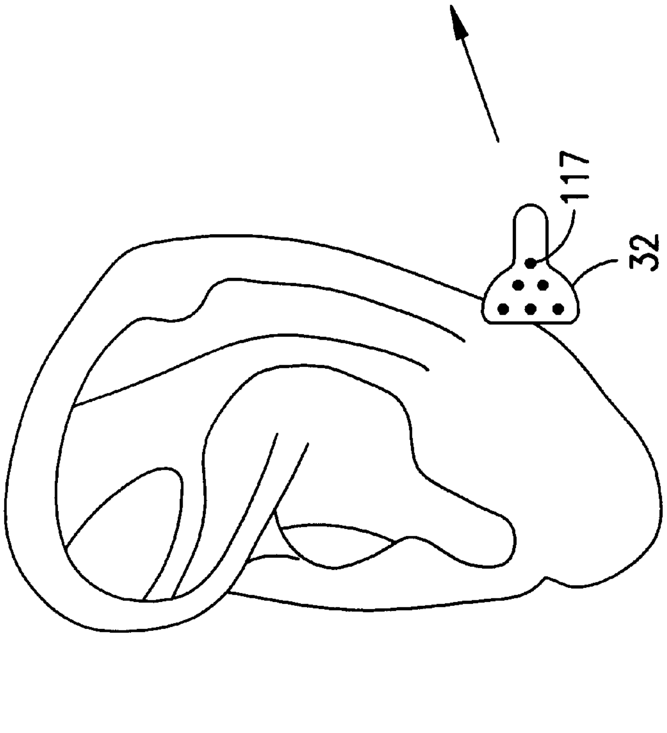

FIG. 43A depicts a side plan view of a human ear, and a device of the invention having orienting margin 32 and orienting protrusion 117; FIG. 42B depicts a side plan view of a human ear with a device of the present invention partially fastened thereto; and FIG. 43C depicts a side plan view of a human ear, with a device of the invention fastened to therapy points on the tragus with orienting margin 32 aligned with the edge of the tragus and orienting protrusion 117 aligned with the tip of the tragus, which can be used to treat smoking, drug or alcohol withdrawal, or to promote weight loss.

Figure 44:
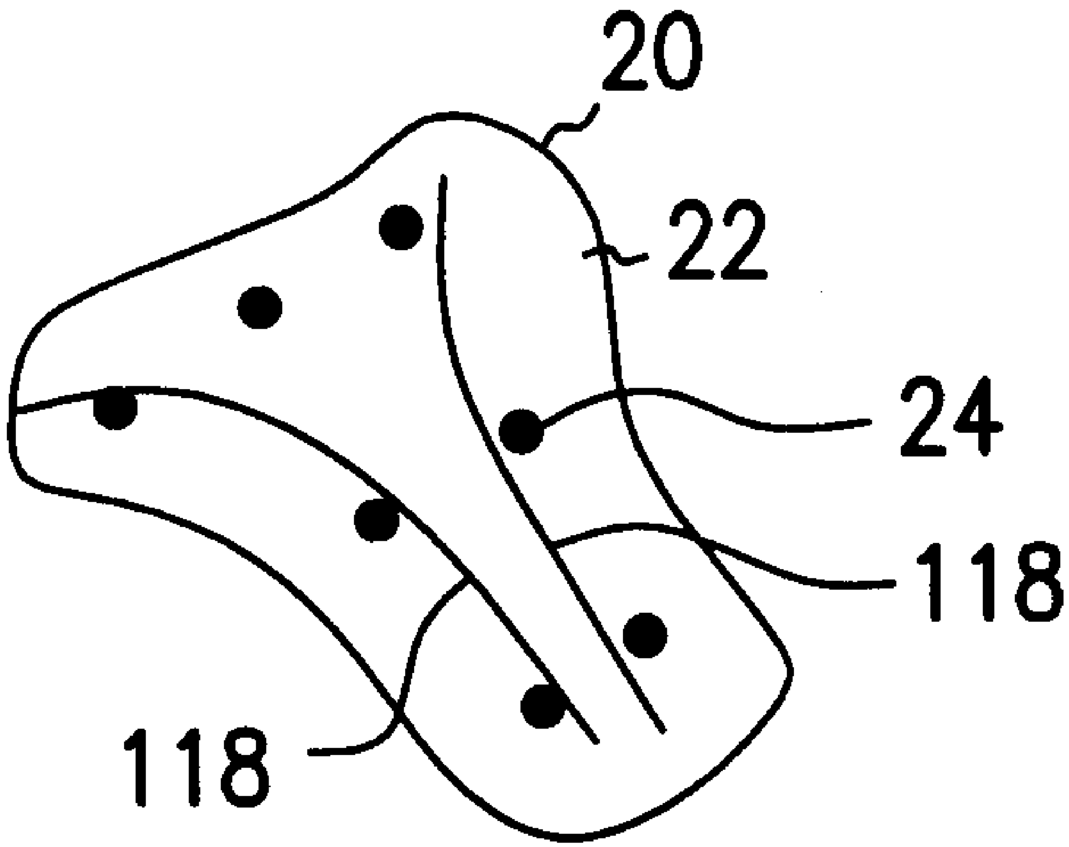
FIG. 44 depicts a device of the invention having an orienting template to align the device over a selected skin surface.

FIG. 44 depicts a device of the invention 20 comprising a base sheet 22 and at least one protrusion 24, having an orienting template 118 printed or embossed on the base sheet to align over the cartilage ridge, which can be used to treat lower back pain or sciatica.

Also contemplated by the present invention, but not depicted, is the addition of a layer of medicament or a medicament that can be mixed or blended into the base sheet material. The layer may be to either surface of the base sheet depending on the material used in the base sheet and film versus weave construction. The medicament is then available to the wearer of the device, for absorption through their skin, as an additional adjunct to the acupressure effects provided by the at least one bead. Examples of useful medicaments include camphor, tiger balm, wintergreen or other pharmacological agents for transdermal or topical use.

Figure 11:
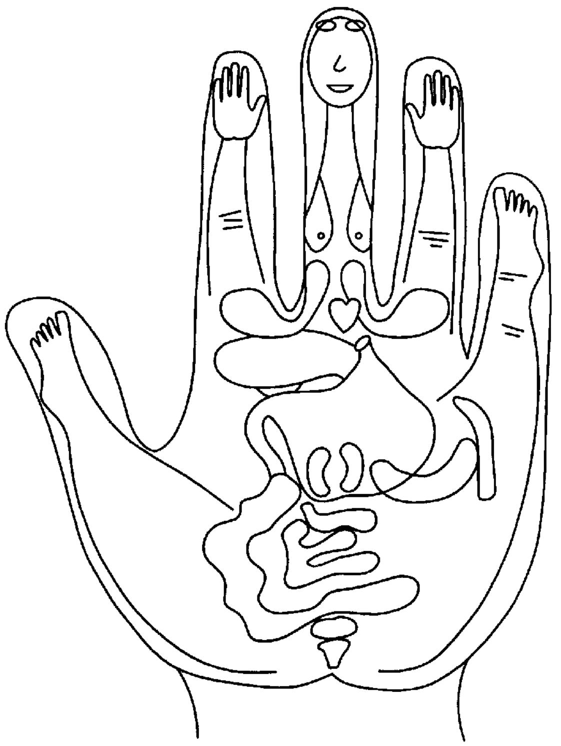
FIG. 11, for reference, depicts a ventral view of a homunculus representation found on the palmar surface of a human hand.
Figure 12:
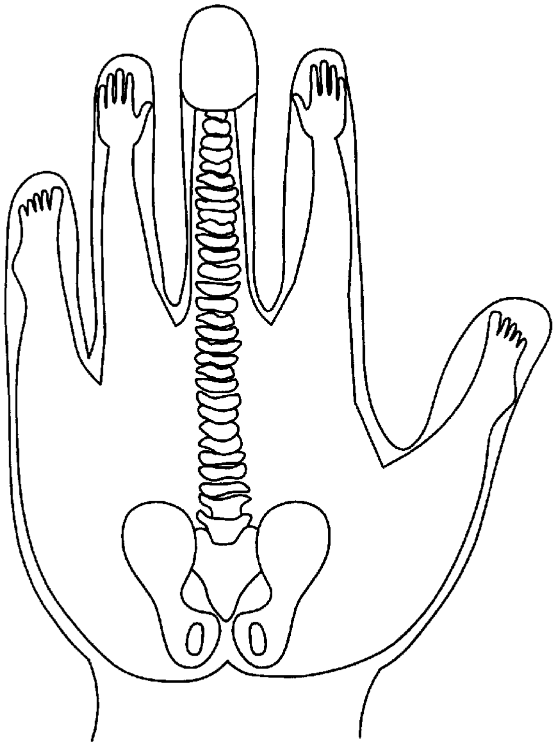
FIG. 12, for reference, depicts a dorsal view of a homunculus representation found on the dorsal surface of a human hand.

The previous description is exemplary of a few of the many embodiments contemplated by the present invention for use on or about the ear. The use of an orienting margin, an orienting protrusion or constellation, or an orienting template can be extended to any surface area of the human body. For example, as shown diagrammatically in FIGS. 11 and 12, the body is represented in homunculus form on the surface of the hand. In FIG. 11, on the palmar surface one notes the representation of the ventral surface and internal organs of the human. In FIG. 12, the dorsal aspect of the body is represented on the extensor surface of the hand. These maps are uniform from one person to the next. The present invention, using an orienting margin, orienting protrusion, orienting constellation, or orienting template concept, provides for any number of acupressure patches that can be placed accurately, and reproducibly, by anyone regardless of level of skill in the art of acupressure.

Figure 13:
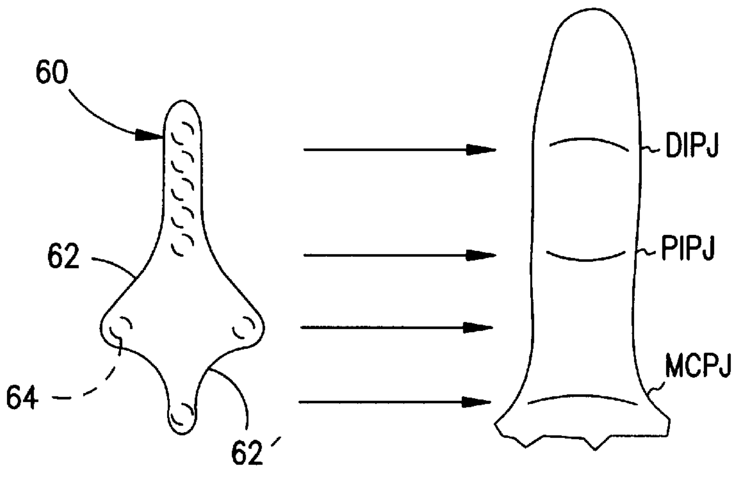
FIG. 13 depicts a top plan view of a further additional embodiment of the present invention aligned with a specific anatomic relationship as shown by the arrows as to where the device is to be placed on the skin.

FIGS. 13–16 depicted representative examples of the various types of embodiments contemplated by the present invention for exploiting the known acupressure and acupuncture sites on the human body. FIG. 13 depicts an acupressure patch 60 having an orienting margin 62,62' and at least one bead 64 shown in phantom as being on the other side of acupressure device 60. Such an acupressure patch is useful for placing beads in a pattern for treating anterior portions of the head, face, neck and upper chest. The pattern of beads used is variable, depending on the area of the body desired to be treated by acupressure to the equivalent homunculus area, and is not a limiting factor in the present invention. Orienting margin 62,62' is used to align acupressure patch 60 to the user's finger. In FIG. 13, orienting margin 62,62' is used to align acupressure patch 60 so orienting margin 62,62' is between the user's metacarpophalangeal joint MCPJ and the proximal interphalangeal joint PIPJ. The several arrows show how the device is moved into place relative to the MCPJ, PIPJ and the distal interphalangeal joint DIPJ. The long axis of acupressure patch 60 is aligned along the midline of the finger.

Figure 14:
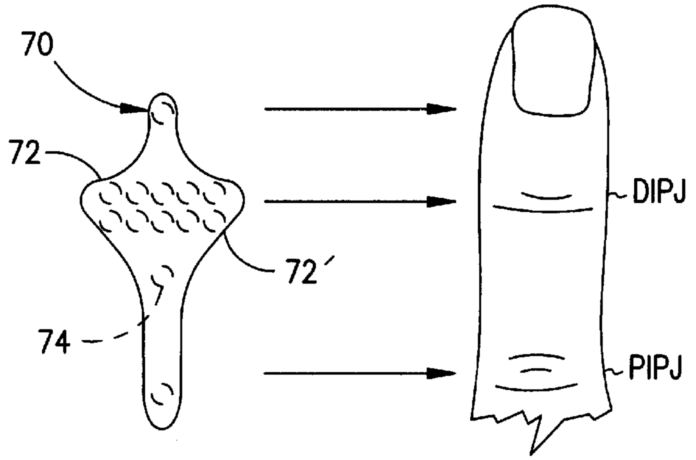
FIG. 14 depicts a top plan view of an another further additional embodiment of the present invention aligned with a specific anatomic relationship as shown by the arrows as to where the device is to be placed on the skin.

FIG. 14 depicts an acupressure patch 70 as an embodiment of the present invention useful for treating disorders associated with the back of the head and spine. Acupressure patch 70 includes an orienting margin 72,72' and at least one protrusion 74. In this embodiment, orienting margin 72,72' is aligned with the plane of the DIPJ on the extensor surface of the user's finger and the long axis of acupressure patch 70 is aligned along the midline of the finger.

Figure 15:
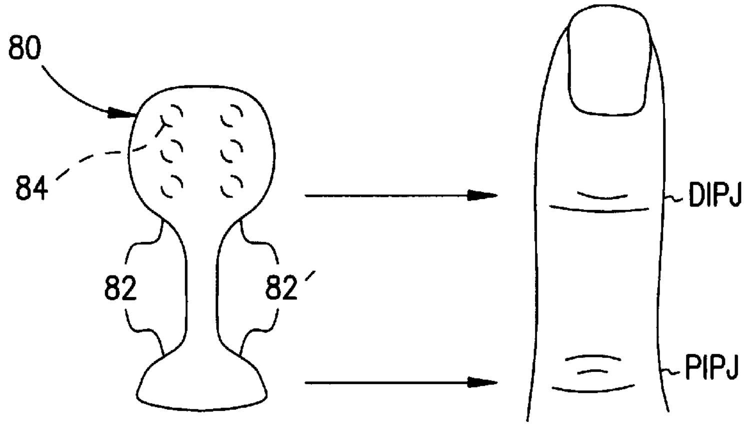
FIG. 15 depicts a top plan view of yet another further additional embodiment of the present invention aligned with a specific anatomic relationship as shown by the arrows as to where the device is to be placed on the skin.

FIG. 15 depicts another variation of an embodiment of the present invention as an acupressure patch 80 having an orienting margin 82,82' and at least one protrusion 84. Orienting margin 82,82' is aligned between two joints, in this example between the PIPJ and the DIPJ. The long axis is again aligned with the midline of the finger.

Figure 16:
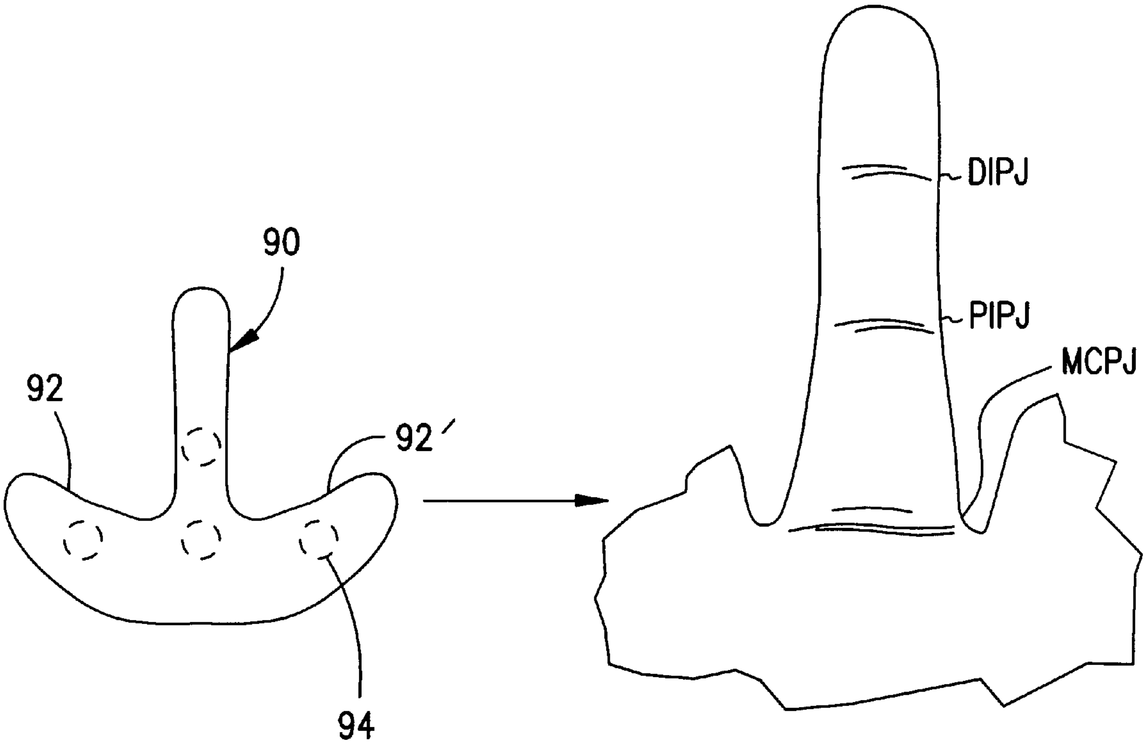
FIG. 16 depicts a top plan view of yet another further additional embodiment of the present invention aligned with a specific anatomic relationship as shown by the arrows as to where the device is to be placed on the skin.

FIG. 16 depicts an acupressure patch 90 having an orienting margin 92,92' and at least one protrusion 94. This embodiment depicts one use of an orienting margin for obtaining alignment of an acupressure patch to the contours of a user's palm. Orienting margin 92,92' is used to align acupressure patch 90 along the midline of a digit, to the MCPJ of that digit, and to the web areas between the digit and the two digits to either side.

There are other areas, including homunculus equivalent areas, elsewhere on the surface of a body. In particular, there are twelve meridians and the homunculi of the feet and nose may also be approached for treatment with a device of the present invention. The number of possible embodiments is extensive and overly burdensome to depict and describe each and every one. The principles of the present invention have been presented and depicted herein.

The foregoing description is considered as illustrative only of the principles of the invention, and since numerous modifications and changes will readily occur to those skilled in the art, it is not the inventor's desire to limit the invention to the exact construction and operation shown and described herein. Accordingly, all suitable modifications and equivalents may be resorted to, falling within the scope of the present invention. All publications, patents, and patent documents are incorporated by reference herein, as though individually incorporated by reference.

What is claimed is:

1. An acupressure device for use on a selected skin surface portion of a human body, the device comprising:

a base sheet having a margin, wherein the margin has at least a portion shaped as an orienting margin which corresponds to a shape on or adjacent to the selected skin surface portion;

at lease one protrusion on the base sheet, and a fastener, wherein said orienting margin positions one or more of said protrusions to one or more therapy points on said body.

2. The device of claim 1, wherein at least one protrusion is embedded in the base sheet.

3. The device of claim 1, wherein at least one protrusion is affixed to the base sheet.

4. The device of claim 1, wherein at least one protrusion is molded from the base sheet.

5. The device of claim 1, wherein the fastener comprises an adhesive layer on a portion of the base sheet or the at least one protrusion.

6. The device of claim 1 wherein the orienting margin is suitable for positioning the protrusions to one or more therapy points on the antitragus, tragus, uterine point, shen men, antidepressent areas, helix, antihelix, scaphoid fossa, triangular fossa, concha, or the cartilage ridge or other area of the pinna.

7. The device of claim 1 wherein the orienting margin corresponds to a shape on or adjacent to a therapy point useful for treating general headaches, migraine headaches, premenstrual syndrome, menstrual cramps, depression, impotency, libido, appetite suppression, low back pain, sciatica, fatigue, chronic fatigue, insomnia, jet lag, stress, anxiety, shoulder pain, neck pain, temporomandibular joint dysfunction (TMJ), jaw pain, smoking, drug or alcohol withdrawal, alcoholism, sinusitus, allergies, asthma, motion or sea sickness, stomach ache, heartburn, indigestion, acid reflux, or nausea.

8. The device of claim 1 for treating premenstrual syndrome or menstrual cramps in a human, wherein the margin has at least a portion shaped as an orienting margin which corresponds to a shape on or adjacent to the triangular fossa, wherein said orienting margin positions the device to one or more therapy points on said triangular fossa.

9. The device of claim 1 for treating smoking, drug or alcohol withdrawal in a human, wherein the margin has at least a portion shaped as an orienting margin which corresponds to a shape on or adjacent to the tragus or concha ridge of a human.

10. The device of claim 1 for treating headache or migraine headache in a human, wherein the margin has at least a portion shaped as an orienting margin which corresponds to a shape on or adjacent to the antitragus, wherein said orienting margin positions the device to one or more therapy points on said antitragus.

11. The device of claim 1, wherein the orienting margin is suitable for positioning the protrusions to one or more therapy points on the tragus.

12. An acupressure device for use on a selected skin surface portion of a human body, the device comprising:

a base sheet;

a plurality of protrusions on the base sheet, wherein the plurality of protrusions is arranged in an orienting constellation having a shape that corresponds to a shape on or adjacent to the selected skin surface portion; and a fastener.

13. The device of claim 12, wherein at least one protrusion is embedded in the base sheet.

14. The device of claim 12, wherein at least one protrusion is affixed to the base sheet.

15. The device of claim 12, wherein at least one protrusion is molded from the base sheet.

16. The device of claim 12, wherein the fastener comprises an adhesive layer on a portion of the base sheet or the plurality of protrusions.

17. The device of claim 12 wherein the orienting constellation is suitable for positioning the protrusions to one or more therapy points on the antitragus, tragus, uterine point, shen men, antidepressent areas, antihelix, scaphoid fossa, or cartilage ridge.

18. The device of claim 8 wherein the orienting constellation corresponds to a shape on or adjacent to a therapy point used to treat a general headaches, migraine headaches, premenstrual syndrome, menstrual cramps, depression, impotency, libido, appetite suppression, low back pain, sciatica, fatigue, chronic fatigue, insomnia, jet lag, stress, anxiety, shoulder pain, neck pain, temporomandibular joint dysfunction (TMJ), jaw pain, smoking, drug or alcohol withdrawal, alcoholism, sinusitus, allergies, asthma, motion or sea sickness, or nausea.

19. The device of claim 12 for treating premenstrual syndrome or menstrual cramps in a human, wherein the plurality of protrusions is arranged in an orienting constellation having a shape that corresponds to a shape on or adjacent to the triangular fossa of a human.

20. The device of claim 12 for treating smoking, drug or alcohol withdrawal in a human, wherein the plurality of protrusions is arranged in an orienting constellation having a shape that corresponds to a shape on or adjacent to the tragus or concha ridge of a human.

21. The device of claim 12 for treating headache or migraine headache in a human, wherein the plurality of protrusions is arranged in an orienting constellation having a shape that corresponds to a shape on or adjacent to the antitragus of a human.

22. The device of claim 12, wherein the orienting constellation is suitable for positioning the protrusions to one or more therapy points on the tragus.

23. An acupressure device for use on a selected skin surface portion of a human body, the device comprising:

a base sheet;

a plurality of protrusions on the base sheet; and a fastener;

wherein one or more protrusions is an orienting protrusion suitable for aligning said plurality to the selected skin surface portion.

24. The device of claim 23, wherein at least one protrusion is embedded in the base sheet.

25. The device of claim 23, wherein at least one protrusion is affixed to the base sheet.

26. The device of claim 23, wherein at least one protrusion is molded from the base sheet.

27. The device of claim 23, wherein the fastener comprises an adhesive layer on a portion of the base sheet or the one or more protrusions.

28. The device of claim 23 wherein the orienting protrusion is suitable for positioning the device to one or more therapy points on the antitragus, tragus, uterine point, shen men, antidepressent areas, antihelix, scaphoid fossa, or cartilage ridge.

29. The device of claim 23 wherein the orienting protrusion is suitable for positioning the device to a therapy point used to treat a general headaches, migraine headaches, premenstrual syndrome, menstrual cramps, depression, impotency, libido, appetite suppression, low back pain, sciatica, fatigue, chronic fatigue, insomnia, jet lag, stress, anxiety, shoulder pain, neck pain, temporomandibular joint dysfunction (TMJ), jaw pain, smoking, drug or alcohol withdrawal, alcoholism, sinusitus, allergies, asthma, motion or sea sickness, or nausea.

30. The device of claim 23 for treating premenstrual syndrome or menstrual cramps in a human, wherein at least one protrusion is an orienting protrusion suitable for position the device to one or more therapy points on the triangular fossa of a human.

31. The device of claim 23 for treating smoking, drug or alcohol withdrawal in a human, wherein at least one protrusion is an orienting protrusion suitable for position the device to one or more therapy points on the tragus or concha ridge of a human.

32. The device of claim 23 for treating headache or migraine headache in a human, wherein at least one protrusion is an orienting protrusion suitable for position the device to one or more therapy points on the antitragus of a human.

33. The device of claim 23, wherein the orienting protrusion is suitable for positioning the device to one or more therapy points on the tragus.

34. An acupressure device for use on a selected skin surface portion of a human body, the device comprising:

a base sheet;

one or more protrusions on the base sheet;

a fastener; and an orienting template on the base sheet suitable for aligning the device to the selected skin surface portion.

35. The device of claim 34, wherein at least one protrusion is embedded in the base sheet.

36. The device of claim 34, wherein at least one protrusion is affixed to the base sheet.

37. The device of claim 34, wherein at least one protrusion is molded from the base sheet.

38. The device of claim 34, wherein the fastener comprises an adhesive layer on a portion of the base sheet or the one or more protrusions.

39. The device of claim 34 wherein the orienting template is suitable for positioning the device to one or more therapy points on the antitragus, tragus, uterine point, shen men, antidepressant areas, antihelix, scaphoid fossa, or cartilage ridge.

40. The device of claim 34 wherein the orienting template is suitable for positioning the device to a therapy point used to treat a general headaches, migraine headaches, premenstrual syndrome, menstrual cramps, depression, impotency, libido, appetite suppression, low back pain, sciatica, fatigue, chronic fatigue, insomnia, jet lag, stress, anxiety, shoulder pain, neck pain, temporomandibular joint dysfunction (TMJ), jaw pain, smoking, drug or alcohol withdrawal, alcoholism, sinusitus, allergies, asthma, motion or sea sickness, or nausea.

41. The device of claim 34 for treating premenstrual syndrome or menstrual cramps in a human, wherein the orienting template positions the device to one or more therapy points on the triangular fossa of a human.

42. The device of claim 34 for treating smoking, drug or alcohol withdrawal in a human, wherein the orienting template positions the device to one or more therapy points on the tragus or concha ridge of a human.

43. The device of claim 34 for treating headache or migraine headache in a human, wherein the orienting template positions the device to one or more therapy points on the antitragus of a human.

44. The device of claim 34, wherein the orienting template is suitable for positioning the device to one or more therapy points on the tragus.

* * * * *

UNITED STATES PATENT AND TRADEMARK OFFICE

CERTIFICATE OF CORRECTION

PATENT NO. : 6,458,146 B1
DATED : October 1, 2002
INVENTOR(S) : Kramer

It is certified that error appears in the above-identified patent and that said Letters Patent is hereby corrected as shown below:

Title Page,
Field [54], Invention, delete "ACUPUNCTURE" and insert -- ACUPRESSURE --, therefor.

Column 1,
Line 1, delete "ACUPUNCTURE" and insert -- ACUPRESSURE --, therefor.

Column 8,
Line 1, delete "a method a method" and insert -- a method --, therefor.

Column 10,
Line 51, delete "appetight" and insert -- appetite --, therefor.

Column 11,
Line 24, delete "may be" and insert -- may --, therefor.

Column 12,
Line 21, delete "also useful" and insert -- also be useful --, therefor.
Line 46, delete "one".
Line 50, delete "constelation" and insert -- constellation --, therefor.

Column 15,
Line 54, delete "appetight" and insert -- appetite --, therefor.

Column 17,
Line 35, delete "lease" and insert -- least --, therefor

UNITED STATES PATENT AND TRADEMARK OFFICE

CERTIFICATE OF CORRECTION

PATENT NO. : 6,458,146 B1
DATED : October 1, 2002
INVENTOR(S) : Kramer

It is certified that error appears in the above-identified patent and that said Letters Patent is hereby corrected as shown below:

Column 18,
Line 40, delete "8" and insert -- 12 --, therefor.

Column 19
Line 7, after "aligning" insert -- the --.

Signed and Sealed this

Eighth Day of June, 2004

JON W. DUDAS
*Acting Director of the United States Patent and Trademark Office*